United States Patent [19]

Oswald et al.

[11] 4,083,803

[45] Apr. 11, 1978

[54] ANCHORED SILYLHYDROCARBYL PHOSPHINE TRANSITION METAL COMPLEX CATALYSTS AND THEIR METHOD OF PREPARATION

[75] Inventors: Alexis A. Oswald, Mountainside; Lawrence L. Murrell, Elizabeth, both of N.J.

[73] Assignee: Exxon Research & Engineering Co., Linden, N.J.

[21] Appl. No.: 610,628

[22] Filed: Sep. 5, 1975

Related U.S. Application Data

[63] Continuation-in-part of Ser. No. 265,507, Jun. 23, 1972, Pat. No. 3,907,852.

[51] Int. Cl.$^2$ ............................................. B01J 31/24
[52] U.S. Cl. ..................... 252/430; 252/428; 252/429 R; 252/431 C; 252/431 N; 252/431 P; 560/231; 260/604 HF; 260/666 P; 260/448.2 R; 260/448.2 B; 210/40
[58] Field of Search ................... 252/428, 429 R, 430, 252/431 C, 431 P, 431 N

[56] References Cited

U.S. PATENT DOCUMENTS

| | | | |
|---|---|---|---|
| 3,389,092 | 6/1968 | Sanford et al. | 252/430 |
| 3,487,112 | 12/1969 | Paulik et al. | 252/431 P |
| 3,726,809 | 4/1973 | Allum et al. | 252/431 P |
| 3,832,404 | 8/1974 | Allum et al. | 252/431 P |

OTHER PUBLICATIONS

Lapporte et al, J. Org. Chem., 28 (July, 1963), pp. 1947–1948.

*Primary Examiner*—Patrick P. Garvin
*Attorney, Agent, or Firm*—Joseph J. Allocca

[57] ABSTRACT

Novel heterogeneous silylhydrocarbyl phosphine transition metal complex catalysts and intermediates therefore are prepared by (a) the selective monoaddition of silane having chlorine, alkoxy or acyloxy groups to an α, ω-diene, (b) followed by the addition of a phosphine to the resulting ω-alkenyl silanes to form the corresponding silylalkyl phosphines, (c) which are then covalently anchored as such or in the form of their transition metal complexes via condensation of their reactive silane substituents with hydroxy groups of silica and metal oxides, (d) optionally followed by complexing the free phosphine groups of anchored silylalkyl phosphines with transition metal compounds.

20 Claims, No Drawings

ANCHORED SILYLHYDROCARBYL PHOSPHINE TRANSITION METAL COMPLEX CATALYSTS AND THEIR METHOD OF PREPARATION

CROSS-REFERENCE TO RELATED CASES

This application is a continuation-in-part of a patent application bearing U.S. Ser. No. 265,507 filed June 23, 1972, now U.S. Pat. No. 3,907,852.

This invention relates to a novel method of anchoring phosphine complexes of transition metals to inorganic solids such as silica for the production of novel catalysts.

The novel method of anchoring is based on the known ability of certain silane compounds to react with the hydroxyl groups of silica and the like (see Plastic Report 18 entitled "Glass/Resin Interface: Patent Survey, Patent List, and General Bibliography", Office of Technical Services, Department of Commerce). The complexing reactions of simple hydrocarbon phosphines with transition metals are also known as well as the use of such complexes in catalysis. (For reference see the monograph of Juergen Falbe, "Carbon Monoxide in Organic Synthesis", Springer-Verlag, New York, 1970.)

The present invention chemically links the reactive silane group and the complex forming phosphine group via a divalent hydrocarbon radical. Such bridged silaphosphines are then anchored and complexed with transition metals to derive new types of catalysts. These catalysts are insoluble and as such, are free from the catalyst recovery problems commonly experienced with the known soluble complexes of phosphines.

The present invention is most closely related to U.S. Pat. No. 3,726,809 on "Catalyst Supports and Transition Metal Catalysts Supported Thereon" by K. G. Allum, S. McKenzie and R. C. Pitkethly. This patent disclosed a similar approach to catalyst anchoring. However, the only catalyst ligand used for anchoring by Allum et al, is 2-triethoxysilylethyl diphenyl phosphine, a known compound:

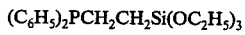

$(C_6H_5)_2PCH_2CH_2Si(OC_2H_5)_3$

Other known silylalkylphosphines which may be represented by the general formula:

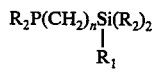

$R_2P(CH_2)_nSi(R_2)_2$
            |
            $R_1$ wherein R is phenyl, ethyl, butyl, $R_1$ is ethoxy, methyl, phenyl and $(R_2)_2$ is ethoxy, chlorine and n is 2 and 3, are described as exemplary anchoring ligands on column 4, lines 4 to 26 of the same patent. All these phosphines have an alkylene bridge having two or three carbon atoms between the silicon and phosphorus.

In the generic disclosure in claim 3 of the Allum et al patent compounds of the formula:

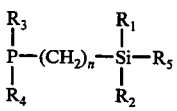

$R_3$       $R_1$
 |           |
P—$(CH_2)_n$—Si—$R_5$
 |           |
$R_4$       $R_2$ wherein $R_1$ and $R_2$ are selected from the group consisting of aryl, alkyl, alkoxy and aryloxy groups containing up to 10 carbons, and halogen, $R_3$ and $R_4$ are selected from the group consisting of aryl and alkyl groups containing up to 10 carbon atoms, $R_5$ is selected from the group consisting of halogen, alkoxy and aryloxy containing up to 10 carbon atoms and n is an integer of from 1 to 6, are presented as possible anchoring compounds. However, in all the working examples and in the description at Column 4, lines 65 to 75 of the U.S. patent, the alkylene bridge between phosphorus and silicon has two or three carbons.

In contrast, the key to the present invention is the synthesis of novel silylalkylphosphine anchoring agents via novel olefinic silanes with new methods. The most important, distinctive property of these novel anchoring agents, hitherto unavailable via known processes, is the longer alkylene bridge connecting the phosphine and silicon moiety. These anchoring agents were converted to anchored transition metal complexes which were found to be superior selective catalysts in the present invention. Such anchored catalysts are also superior to similar transition metal complex catalysts anchored to organic polymers, e.g. macroreticular resins. The superiority of the present catalysts is largely due to the stability and the high surface to weight ratio of the inorganic solids they are attached to.

In the subsequent detailed discussion of our invention, the synthesis of substituted silylalkylphosphine anchoring agents via silane-diene monoaddition followed by phosphine addition will be considered at first. Anchoring reactions with silica and the like and complexing with transition metals will be described thereafter. Finally, novel processes using the anchored catalysts will be discussed. For the details of some of the working examples, reference is made to the parent application, U.S. Ser. No. 265,507, now U.S. Pat. No. 3,907,852.

1. Addition of Silanes to the α,ω-Dienes

The addition of silanes, containing the reactive Si-H functionality, to monoolefins is well known. For reference, see the monograph by C. Eaborn entitled "Organosilicon Compounds", Academic Press, New York, 1970, pages 45–64. However, the addition of silanes to α,ω-dienes is complicated by the tendency of terminal vinylic groups to isomerize into internal olefinic groups during the addition.

It was found in the present invention that chlorosilanes can be added selectively to α,ω-dienes in a selective terminal manner to yield novel ω-alkenyl silane monoadducts and bis-α,ω-silyl alkanes.

The silane reactants are preferably of the general formula:

$R_{4-y}SiH_y$ wherein R is chlorine; $C_1$ to $C_4$ alkoxy such as methoxy, ethoxy, propoxy; $C_1$ to $C_4$ acyloxy such as acetoxy; R can also be a $C_1$ to $C_6$ saturated aliphatic or aromatic hydrocarbyl such as phenyl, methyl providing that at least one of the R groups is a reactive chlorine, alkoxy or acyloxy group; y is 1 and 2. The reactive R is preferably chlorine or acyloxy, most preferably chlorine. It is preferred that all R groups by reactive.

The α,ω-diene reactants of the present invention are of the general formula:

$CH_2=CH(CH_2)_kCH=CH_2$ wherein k is 1 to 26, preferably 4 to 26, more preferably 4 to 10, most preferably 6 to 10.

Exemplary reactants are trichlorosilane, triethoxysilane, triacetoxysilane, methyldichlorosilane, phenylchlorosilane, 1,4-pentadiene, 1,21-docosadiene, 1,13-tetradecadiene.

It was found that these reactants yield selectively ω-alkenyl silanes and bis α,ω-silyl alkanes according to the following schemes:

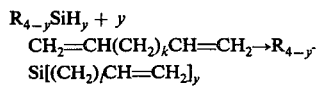
$$CH_2=CH(CH_2)_kCH=CH_2 \rightarrow R_{4-y}Si[(CH_2)_lCH=CH_2]_y$$

wherein $y$ is 1 and 2 and $l$ is $k + 2$ and $$R_3SiH + CH_2=CH(CH_2)_kCH=CH_2 \rightarrow R_3Si(CH_2)_lCH=CH_2 + R_3Si(CH_2)_mSiR_3$$

wherein $m$ is $k + 4$.

Such additions are preferably carried out in the liquid phase in the presence of free radical and/or metal and/or metal salt catalysts. Exemplary free radical catalysts are radiation such as ultraviolet light and gamma rays, chemicals such as peroxide compounds and azo compounds and thermal catalysis by heating. Exemplary metal catalysts are for example, platinum, palladium, usually on either asbestos or alumina or charcoal. Illustrations for metal salt catalysts are potassium chloroplatinate, chloroplatinic acid, ruthenium chloride. These metal salts can be also used as their complexes, for example with trihydrocarbyl phosphines.

The temperature of these additions may vary from −90° C. to 200°, preferably −90° to 90° C., most preferably from −90° to 30° C. The temperature may be critical with regard to selective monoaddition to yield ω-alkenyl silanes.

The ratio of the reactants may vary from 0.5 to 6 moles of diolefin per mole of silane. It is, however, preferred for a selective monoaddition to use 2 to 6 moles of diolefin per mole of silane.

The additions are carried out to a substantial conversion and the products are then isolated usually by fractional distillation.

The ω-alkenyl silane monoadducts have properties unexpectedly different from the known vinyl and allyl silanes of analogous structure. The chloro derivatives are more reactive in Ziegler-type polymerization. These terminally unsaturated compounds behave also very differently from their internally unsaturated isomers. The terminal olefinic group of these compounds, for example, is reactive towards phosphine adding agents while the internal compounds are inert.

The bis-α,ω-silyl alkanes are useful as crosslinking reagents due to their diterminal functionality. As such they may find particular applications in adhesives, mastics and the like.

2. Addition of Phosphines to Alkenyl Silanes

The addition of phosphines to vinylsilanes has been extensively studied by H. Niebergall. (See Makromolekulcare Chemie, Volume 52, pages 218–229, which was published in 1962). He has found that diethyl phosphine reacts with divinyl dichlorosilane as shown by the following reaction schemes:

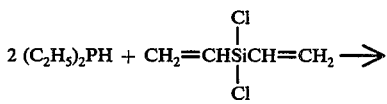

-continued

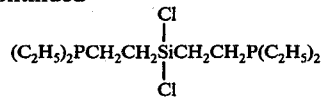

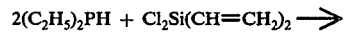

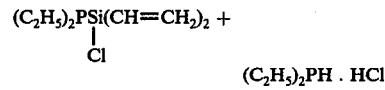

$(C_2H_5)_2PH \cdot HCl$

Niebergall reported that both of the above reactions occur under free radical conditions.

In the present work, it was surprisingly found that in the reaction of phosphines with ω-alkenyl silanes, the formation of P-Si bonds can be avoided. As such the reaction could be used, preferably under mild conditions, for the synthesis of novel ω-silylalkyl phosphines.

The phosphine adding agent is of the general formula:

wherein R' is a $C_1$ to $C_{30}$ saturated aliphatic or aromatic hydrocarbyl radical selected from the group consisting of alkyl, cycloalkyl, phenylalkyl, phenyl, alkylphenyl. R' is preferably $C_1$ to $C_{30}$ alkyl, cyclohexyl and phenyl, most preferably $C_1$ to $C_4$ alkyl, cyclohexyl and phenyl. The symbol $x$ stands for numbers 1–3, preferably 1–2.

The ω-alkenyl silane reactants are of the general formula:

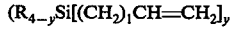

wherein the meaning of the symbols is the same as in part 1. of the disclosure.

The reaction of the above phosphines with the ω-alkenyl silanes according to the present invention involves only the P—H and CH$_2$=CH—Si groups as shown by the following reaction equation:

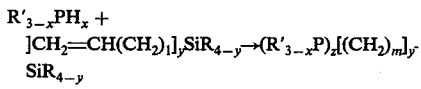

wherein the meaning of old symbols is the same as before. The new symbol $z$ is a number from 1–3. The value of $z$ is, of course, selected so as to satisfy the valence relationships.

Preferred additions and compositions are those wherein $x$ and $y$ are 1 and 2, for example $$R'_2PH + CH_2=CH(CH_2)_lSiR_3 \rightarrow R'_2P(CH_2)_mSiR_3$$

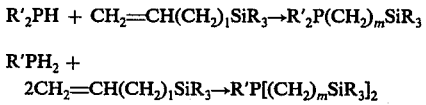

Specifically preferred are ω-alkenyl chlorosilane and acyloxysilane reactants and compositions resulting therefrom, e.g.

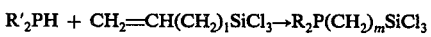

The desired anti-Markovnikov-type reaction is initiated by the use of free radical catalysts such as radiation and/or chemical initiators. Initiation by radiation includes gamma rays and ultraviolet light. Typical chemical initiators are azo compounds such as azo-bisisobutyronitrile. The use of irradiation and its combination with chemical initiation are preferred over the use of chemical initiation alone. Radiation means of initiation allow the use of low reaction temperatures.

The temperature of the reaction is between −105° and +100° C., preferably between −100° and +16° C., most preferably between −80° C. and 0° C. The highest allowed reaction temperature is largely dependent on the basicity of the phosphine used. The more basic dialkyl phosphines have a higher tendency to undergo undesirable side reactions involving the chlorosilane groups.

The reaction is to be carried out in the liquid state. This means that the process is normally atmospheric. In the case of phosphines which are normally gaseous at the reaction temperature, such as methylphosphine, superatmospheric pressures up to 20 atmospheres may be used to keep the reactants in the liquid phase.

The reaction is usually carried out without added solvents. At times, however, nonreactive solvents can be advantageously used. Preferred solvents include ketones such as methyl ethyl ketone, ethers and thioethers such as dipropyl sulfide, aliphatic and cycloaliphatic hydrocarbons such as cyclohexane, aromatic hydrocarbons and their halogenated derivatives such as chlorobenzene.

The ratio of reactants is not critical. The reactants are usually employed in equivalent quantities. However, it is preferred to have 0.3 to 6 moles of phosphine per mole of alkenyl silane. In the case of monofunctional reactants, the use of 1.5 to 2.5 mole of phosphine per mole of alkenyl silane is preferred.

The addition reactions are preferably run to a 20 to 90% conversion of the phosphine. The preferred conversion is in excess of 50%. High reactant conversions can be important for avoiding undesired side reactions. At the completion of the reaction, the unreacted components are removed, usually by vacuum stripping. The products can be purified, preferably by fractional distillation in vacuo.

3. Silylhydrocarbyl Phosphine — Transition Metal Complexes

It was found in the present invention that transition metal salts complex with silylhydrocarbyl phosphines of the general formula:

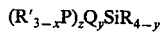

wherein Q is $C_5$ to $C_{30}$, preferably $C_8$-$C_{30}$, saturated aliphatic or aromatic hydrocarbylene such as phenylene, xylylene, terphenylene, preferably $(CH_2)_p$ with $p$ being 5-30, more preferably $p$ equals 8-30, preferably 8 to 14. The meaning of the other symbols is the same as listed in the previous part of this specification. In effect, one of the preferred formula of the silylhydrocarbyl phosphines is as listed there

Compounds of the above and similar more preferred formula react with transition metal compounds such as those of Groups VI, VII and VIII, e.g. of Fe, Ru, Os, Rh, Ir, Ni, Co, Pd and Pt of the formula

wherein M is the metal, X is an anion such as chlorine, bromine, acetate or organic ligand which satisfy the coordination sites of the metal; $n$ is 2 to 6.

Preferred metal compounds contain a readily displaceable organic ligand such as carbonyl, monoolefin, diolefin, tetrahydrofuran, pyridine, acetonitrile. Other preferred metal compounds are capable of raising their coordination number, e.g. nickel-1,5,9-cyclododecatriene.

In a most general way, the novel silylhydrocarbyl phosphine-transition metal complexes can be defined by the following formula:

$$[(R'_{3-x}P)_zQ_ySiR_{4-y}]_g \cdot (MX_n)_s$$

wherein $g$ is 1 to 6, $s$ is 1–3.

For the purposes of discussing the metal complex formation with silylhydrocarbyl phosphines, compounds having $x$, $y$, $z$ equal 1 are selected for illustration, e.g.

$$R'_2PQSiR_3 \text{ and } R'_2P(CH_2)_mSiR_3$$

These compounds and the like are designated L, as monophosphines of a particular structure.

The transition metal complexes may contain various numbers of phosphine ligands as indicated by the formula:

$$L_r \cdot MX_n$$

wherein $n$ and $r$ are 1-6 providing that $n + r$ is 2 to 6, preferably 4.

A preferred example of these metal complexes can be formed from diene-rhodium chloride complex dimers such as that of 1,5-cyclooctadiene i.e. 1,5-COD:

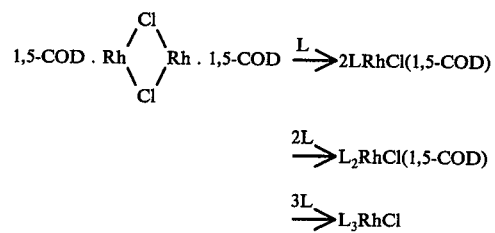

As indicated by the above scheme, the structure of the complexes is dependent on the ratio of the reactants. In general, no reactant is to be used above the stoichiometric quantity.

The complexing reactions are usually dependent on the temperature used. Of course, the practical temperatures are below the decomposition temperature of the complex formed. The temperature is preferably in the range of −90° to 200° C.

The reactions are preferably carried out in the liquid phase in the presence of inert solvents. Hydrocarbons such as paraffins, aromatics and their chlorinated derivatives may be used. Ethers such as tetrahydrofuran can be also suitable. Reactions using volatile transition metal compounds such as nickel tetracarbonyl can be also carried out in the vapor phase.

The novel complexes are usually soluble in hydrocarbons and can be used in solutions. However, they can be also isolated by crystallization or the removal of the solvent by distillation.

4. Anchoring of Silylhydrocarbyl Phosphines and Transition Metal Complexes Thereof The novel phosphine ligands of the present invention and their metal salt complexes can be reacted with the hydroxyl groups of solid, insoluble inorganic compositions, such as those present on the surface of dehydrated silica and metal oxides, e.g. titanium oxide and aluminum oxide. These hydroxyl groups may be covalently bound to silicon or aluminum or may come from coordinatively bound surface water. Whatever their exact bonding may be, reaction of these hydroxyl groups with the chlorosilane groups of the phosphine ligand occurs with the formation of HCl.

Materials which contain or can be made to contain free silanol, i.e. Si—OH groups include various forms of diatomaceous earth, e.g. the well known chromosorbs in gas liquid chromatography, silica gels, silica beads, glass beads.

The anchoring reactions of the reactive silane functions of the present phosphines establish a silicon oxygen bond as indicated by the following schemes:

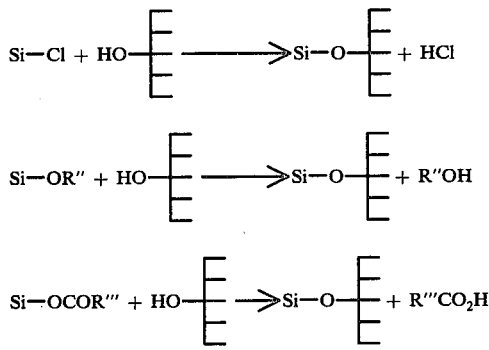

wherein R" is a $C_{1-4}$ alkyl and R''' is a $C_{1-3}$ alkyl or hydrogen. R''' is most preferably methyl.

Since the silyl groups of our phosphines may contain 1 to 3 of the above reactive groups, more than one of them may react per molecule. Concurrent with the anchoring or preferably subsequently some of these reactive groups may be hydrolyzed by water which converts them to silanol groups. The latter may undergo siloxane type condensation, e.g.

$$2\ Si—OH \rightarrow Si—O—Si + H_2O$$

The general scheme of anchoring can be depicted by the following scheme:

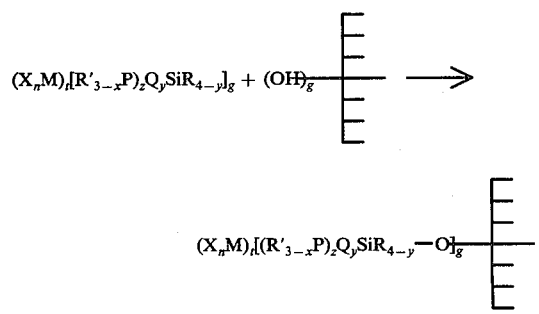

wherein $t = 0-3$.

The anchoring reaction results in the formation of Si—O bonds as illustrated by the following example:

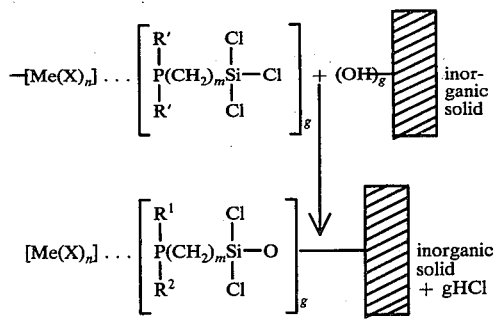

The anchoring reaction can be carried out in a broad temperature range from $-50°$ to $+400°$ C, preferably from $-20°$ to $200°$ C. In the case of dehydrated silica it was surprisingly found that anchoring occurs at low temperatures in the order of $-50°$ to $+50°$ C.

The anchoring reactant is best applied in a solvent. It can be used by impregnation onto silica. In the case of dehydrated silica or undehydrated silica, about one silyl group can be anchored per 50 $A°^2$ of the surface. This corresponds to a complete surface coverage. For the present silylhydrocarbyl phosphines, it is preferred to have less than about 50% surface coverage in order to derive more effective catalysts.

Under the preferred conditions of the present invention, when an ω-trichlorosilylalkyl phosphine is anchored by impregnating silica with its solution in an inert solvent, fewer than three of the chlorine atoms per anchored phosphine group are detached from the silica. The chlorine left can be subsequently removed by extraction using a reactive solvent such as boiling methanol. However, it is pointed out that the degree of primary chloride elimination from the trichlorosilane group is higher if the polymethylene moiety bridged to the phosphine contains a higher number of carbon atoms.

In the present invention, when silica having $1.5 \times 10^{-3}$ mole equivalents of silanol per gram is used, about $0.8 \times 10^{-3}$ mole phosphine or its equivalent phosphine complex was anchored per gram silica. According to a preferred embodiment of the present process, the anchoring is carried out using 0.8 m mole or less, preferably less phosphine per g. of such a silica. In general, the phosphine is preferably used in equivalent or less amounts to react with the hydroxyl groups of silica or other inorganic solids. In contrast the earlier referred Allum et al patent used the anchoring phosphine in severalfold excess.

If the anchoring is carried out with the silylhydrocarbyl phosphines, complexing with the transition metal compounds can be carried out subsequently. The anchored phosphines undergo complex formation with transition metal compounds in the same manner the non-anchored parent phosphines do. However, it is pointed out that using the anchored phosphines stable transition metal complexes can be prepared which are otherwise unstable or unavailable. Covalent anchoring of the phosphine to the inorganic support inhibits ligand interchange and allows the synthesis of novel complexes having a one-to-one phosphine to metal ratio. Complexes having a one-to-three ratio were also prepared as exemplified by the following reaction schemes starting with the 1,5-cyclooctadiene rhodium chloride dimer and anchored phosphines (L):

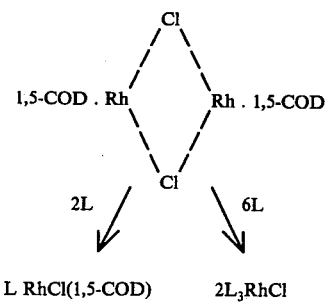

L RhCl(1,5-COD)  2L₃RhCl

The Allum et al patent described only the preparation of complexes having a two-to-one phosphine rhodium ratio.

5. Properties of Anchored Silylhydrocarbyl Phosphines and Transition Metal Complexes Thereof.

The anchored phosphines of the present invention may be used in the field of separations for reversible complexing with acids, metal salts and the like.

The metal complexes of the anchored phosphines represent a novel type of catalysts. These anchored catalysts act in the same manner soluble organometallic catalysts do. They catalyze the same reactions. However, due to their insolubility our catalysts are suited for continuous operations. Catalyst losses can be drastically reduced using our anchored complexes. Another advantage of anchoring resides in the potentially increased stereoselectivity of our catalysts. The approach of reactants to the anchored complex catalyst can occur only from the non-anchored side.

For reference on transition metal phosphine complex catalysts see "Homogeneous Catalysis," No. 70 in the Advances in Chemistry Series of the American Chemical Society and a monograph by J. P. Candlin, K. A. Taylor and D. P. Thompson entitled "Reactions of Transition Metal Complexes," Elsevier, New York, 1968. Anchored ω-trichlorosilylalkyl phosphine-rhodium complexes with different polymethylene chain lengths have differing catalytic activity. For example, L₃RhCl complexes where L represents an anchored phosphine with a dimethylene bridge, is not a hydroformylation catalyst, whereas where L is a C₈ or C₁₄ polymethylene chain, the L₃RhCl catalyst is an active hydroformylation catalyst. Further, the (1,5-cyclooctadiene) LRhCl complex where L represents an anchored phosphine with dimethylene bridge is also not a hydroformylation catalyst, whereas where L is a C₈ or C₁₄ polymethylene chain, the (1,5-cyclooctadiene)LRhCl complexes are active hydroformylation catalysts.

In the case of trialkyloxy- and triacyloxysilylated phosphines the length of the polymethylene group similarly influences the catalytic activity of the anchored phosphines.

The catalytic activity was also dependent on the phosphine coordination number at the metal center, i.e., L to Me ratio, in a selective manner. For example, in the catalysis of hydroformylation reactions, the lower the coordination number, the more active the catalyst. In contrast, for hydrogenation anchored complexes having the highest coordination number have the maximum activity.

Anchored catalysts particularly palladium complexes were also effective for the carbonylation of arylmercury acyloxylates such as the trifluoroacetate in the presence of alcohol, i.e., methanol, to form aromatic esters, e.g., methyl benzoate.

Anchored catalysts can be repeatedly recycled from a batch catalytic reaction without loss in catalytic activity. For example, L₃RhCl were L represents an anchored phosphine with a C₈ methylene chain showed no decrease in hydrogenation activity after being repeatedly recycled.

It can be concluded that metal loss from these novel heterogeneous catalysts is not observed under corrosive solvent and severe reaction conditions.

A. Synthesis of Alkenyl Silanes

Example 1 — Addition of Trichlorosilane to 1,7-Octadiene in the Presence of Chloroplatinate

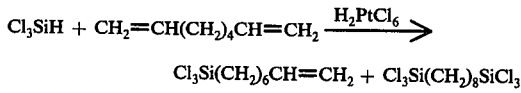

$$Cl_3Si(CH_2)_6CH=CH_2 + Cl_3Si(CH_2)_8SiCl_3$$

A. To a stirred mixture of 27.1 g (0.2 mole) trichlorosilane and 66 g (0.6 mole) 1,7-octadiene in a round bottom flask, is added 0.1 ml of a 10% ethanolic solution of 40% hexachloroplatinic acid. The reaction mixture was heated up to 130° C and kept there for 28 hours to complete the addition. Thereafter, the mixture was fractionally distilled to obtain 49 g, i.e., 70% yield of the 8-octenyl trichlorosilane monoadduct as a colorless liquid boiling between 51°–53° at 0.3 and 6 g of the 1,8-bis-trichlorosilyloctane diadduct as a distillation residue. Analyses. Calcd. for the monoadduct, $C_8H_{17}SiCl_3$: C, 39.11; H, 6.16; Cl, 43.35. Found: C, 39.34; H, 5.72; Cl, 42.44. A proton magnetic resonance (nmr) spectrum of the product shows the characteristic complex resonance signals of the terminal —CH=CH₂ group.

B. A mixture of 108.4 g (0.8 mole) trichlorosilane and 264 g (2.4 mole) 1,7-octadiene was similarly reacted after the addition of 0.4 ml 10% ethanolic solution of 40% chloroplatinic acid by heating the mixture at 50° C for 44 hours. A subsequent fractionation in vacuo yielded 154 g, i.e., 80% of the monoadduct and 20 g, i.e., 10% of the diadduct as a colorless liquid distilling at 123°–125° at 0.4 mm pressure.

Analysis: Calcd. for the diadduct, $C_8H_{16}Si_2Cl_6$: C, 25.21; H, 4.23; Cl, 55.82. Found: C, 24.71; H, 4.00; Cl, 54.64.

An nmr spectrum of the product shows only CH₂ absorptions, indicating a straight chain octamethylene structure.

C. In another experiment, 220 g (1.62 mole) trichlorosilane was added slowly in 20 minutes to a stirred mixture of 660 g (6 mole) 1,7-octadiene at 35° C. Subsequently, the reaction mixture was heated at 50° C for 24 hours to complete the addition and then fractionally distilled. This resulted in 322 g, i.e., 82%, 7-octenyl trichlorosilane and 24 g, i.e., 12%, 1,8-bis-trichlorosilyl octane.

D. When 0.015 ml of the ethanolic chloroplatinic acid was added to a mixture of 3.4 g (0.025 mole) trichlorosilane and 5.5 g (0.05 mole) 1,7-octadiene and the reaction mixture heated at 50° C for 18 hours, a similar addition took place without a double bond isomerization.

E. Similarly, addition without isomerization occurred when the above reactant mixture was allowed to stand at ambient temperature in the presence of 0.015 ml added 10% isopropanol solution of 40% chloroplatinic acid as a catalyst.

Example 2 — Addition of Trisubstituted Silanes to α,ωDienes

In a manner, similar to that described in the first example, a number of trisubstituted silanes were added to a variety of α,ω-diolefins (Table I) to obtain the corresponding ω-alkenyl and internal silanes monoadducts shown in Table II and α,ω-bis-silylalkanes shown in Table III. The terminal versus internal position of the double bonds of the monoadducts and the saturated alkylene structure of the diadducts were shown by now.

In general, small concentrations of hexachloroplatinic acid (about 0.05 mole %) were found to be effective and selective catalysts for such reactions at ambient temperatures. The yield of mono- versus diadducts could be increased by using an excess of the diolefin reactant (Table I).

The mono- and diadduct products are, in general, colorless liquids which were separated by fractional distillation in vacuo (Tables II and III).

Example 3 — Addition of Trichlorosilane to 1,13-Tetradecadiene with Ultraviolet Irradiation A stirred mixture of 6.8 g (0.05 mole) trichlorosilane and 19.6 g (0.1 mole) 1,13-tetradecadiene was irradiated in a closed quartz tube at 45° C for 72 hours with two Hanau 70 watt high pressure mercury immersion lamps, emitting a broad spectrum of ultraviolet light. The resulting crude product was then fractionated to yield 5 g (25%) of 13-tetradecenyl trichlorosilane as the monoadduct.

Example 4 — Reaction of 7-Octenyl Trichlorosilane with Methanol

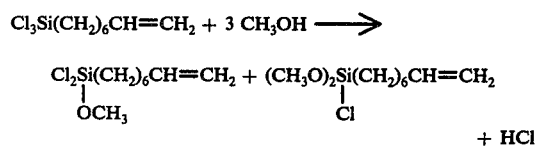

To 246 g (1 mole) stirred 7-octenyl trichlorosilane was added 48 g (1.5 mole) methanol under $N_2$. The

TABLE I

ω-ALKENYL SILANES BY THE ADDITION OF SILICON HYDRIDES TO α, ω-DIENES $$R_3SiH + CH_2=CH(CH_2)_nCH=CH_2 \xrightarrow{H_2PtCl_6} R_3Si(CH_2)_{n+2}CH=CH_2 [+ R_3Si(CH_2)_{n+4}SiR_3]$$

| Ref. No. | Diene, n | Silane, $R_3SiH$ | Diene per Silane Mole Ratio | Max. Reaction Temp. °C. | Reaction Time, Hours | Yield of Dist'd Mono-Adduct, % | Yield of Dist'd Diadduct |
|---|---|---|---|---|---|---|---|
| 1 | 4 | $Cl_3SiH$ | 3 | 130 | 28 | 70 | |
| 2 | | $Cl_2Si(CH_3)H$ | 3 | 115 | <1 | 70 | 14 |
| 3 | | $(C_2H_5O)_3SiH$ | 3 | 50 | 24 | 79 | 10 |
| 4 | 2 | $Cl_3SiH$ | 3 | 50 | 65 | 90 | 4.5 |
| 5 | | $(C_2H_5O)_3SiH$ | 1 | 50 | 24 | 44 | 39 |
| 6 | 2* | $Cl_3SiH$ | 1 | 55 | 18 | 57 | |
| 7 | | $(C_2H_5O)_3SiH$ | 1 | 70 | <1 | 88 | |
| 8 | 10 | $Cl_3SiH$ | 2 | 30 | 2 | 41 | |
| 9 | | $Cl_3SiH$ | 1 | 70 | <1 | 70** | 30 |
| 10 | 6 | $Cl_3SiH$ | 5/3 | 130 | | 41 | 10 |

*Instead of 1,5-hexadiene, 1,4-hexadiene was used as a starting material.
**The terminal double bond of the adduct was isomerized to an internal position during the process.

TABLE II

SOME PHYSICAL AND ANALYTICAL DATA OF SUBSTITUTED ALKENYL SILANES

| Ref. No. | Chemical Structure | Boiling Range ° C/mm | Calcd. C | Calcd. H | Calcd. Cl | Found C | Found H | Found Cl |
|---|---|---|---|---|---|---|---|---|
| 1 | $CH_2=CH(CH_2)_6SiCl_3$ | 51–53/0.3 | 39.11 | 6.16 | 43.35 | 39.34 | 5.72 | 42.44 |
| 2 | $CH_2=CH(CH_2)_6Si(CH_3)Cl_2$ | 50–52/01.? | 47.99 | 8.05 | | 47.62 | 7.82 | |
| 3 | $CH_2=CH(CH_2)_6Si(OC_2H_5)_3$ | 65–68/0.05 | 61.26 | 11.02 | — | 61.58 | 10.57 | — |
| 4 | $CH_2=CH(CH_2)_6Si(OCH_3)_2Cl$ | 60–62/0.1 | 50.72 | 10.41 | | 50.50 | 9.52 | |
| 5 | $CH_2=CH(CH_2)_6Si(OCH_3)_3$ | 48–49/0.1 | 56.85 | 10.41 | — | 55.72 | 9.53 | — |
| 6 | $CH_2=CH(CH_2)_4SiCl_3$ | 33–34/0.7 | 33.12 | 5.10 | | 33.10 | 4.74 | |
| 7 | $CH_3CH=CH(CH_2)_3SiCl_3$ | 38–39/0.1 | 33.12 | 5.10 | 48.88 | 32.51 | 4.83 | 47.87 |
| 8 | $CH_2=CH(CH_2)_4Si(OC_2H_5)_3$ | 55–56/0.15 | 58.47 | 10.64 | — | 58.56 | 10.50 | — |
| 9 | $CH_3CH=CH(CH_2)_3Si(OC_2H_5)_3$ | 48–50/0.15 | 58.47 | 10.64 | | 59.14 | 10.12 | |
| 10 | $CH_2=CH(CH_2)_{12}SiCl_3$ | 103–105/0.05 | 50.98 | 8.25 | 32.25 | 50.80 | 7.80 | |
| 11 | $n-C_{14}H_{27}SiCl_3$ | 123–125/0.3 | 50.98 | 8.25 | 32.25 | 51.54 | 8.31 | 33.04 |
| 12 | $n-C_{10}H_{19}SiCl_3$ | 73–75/0.2 | 43.88 | 7.00 | 38.86 | 44.53 | 6.50 | 39.16 |

TABLE III

SOME PHYSICAL AND ANALYTICAL DATA OF α, ω-BIS-SUBSTITUTED SILYL ALKANES

| Ref. No. | Chemical Structure | Boiling Range ° C./mm | Calcd. C | Calcd. H | Calcd. Cl | Found C | Found H | Found Cl |
|---|---|---|---|---|---|---|---|---|
| 1 | $Cl_3Si(CH_2)_8SiCl_3$ | 123–125/0.4 | 25.21 | 4.23 | 55.82 | 24.71 | 4.00 | 54.64 |
| 2 | $Cl_2Si(CH_3)(CH_2)_8Si(CH_3)Cl_2$ | 125–126/0.2 | 35.30 | 6.52 | | 36.16 | 6.44 | |
| 3 | $(C_2H_5O)_3Si(CH_2)_8Si)OC_2H_5)_3$ | 140–141/0.1 | 54.75 | 10.57 | — | 54.34 | 10.47 | — |
| 4 | $Cl_3Si(CH_2)_6SiCl_3$ | 96–98/0.25 | 21.2 | 3.40 | | 21.20 | 3.40 | |
| 5 | $(C_2H_5O)_3Si(CH_2)_6Si)OC_2H_5)_3$ | 127–128/0.15 | 52.64 | 10.31 | — | 53.29 | 10.21 | |
| 6 | $Cl_3Si(CH_2)_{14}SiCl_3$ | 172–175/0.3 | 36.14 | 6.07 | 45.72 | 36.75 | 5.84 | 44.63 |
| 7 | $Cl_3Si(CH_2)_{10}SiCl_3$ | 121–123/0.1 | 29.35 | 4.93 | | 30.35 | 4.69 | | addition resulted in HCl evolution and some liquid phase separation. Subsequent heating at 65° C for 17 hours resulted in a dark homogeneous liquid. This was fractionally distilled in a vacuo to yield 119 g. colorless liquid 7-octenyldimethoxy chlorosilane at 60°-62° C. under 0.1 mm pressure.

Analysis, Calcd. for $C_{10}H_{21}ClO_2Si$: C, 50.72; H, 10.41. Found: C, 50.50; H, 9.52.

The nmr spectrum shows the presence of two methoxy groups per terminal vinylic group, as expected for the assumed structure.

Example 5 — Reaction of 7-Octenyl Trichlorosilane with Sodium Methoxide

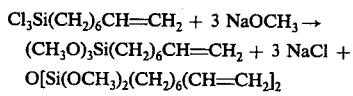

$Cl_3Si(CH_2)_6CH=CH_2 + 3\ NaOCH_3 \rightarrow$
$(CH_3O)_3Si(CH_2)_6CH=CH_2 + 3\ NaCl +$
$O[Si(OCH_3)_2(CH_2)_6(CH=CH_2)]_2$ To a stirred 25% methanolic solution of 33.2 g (0.63 mole) sodium methoxide, is added 50.2 g (0.21 mole) 7-octenyl trichlorosilane with cooling below 50° C. The crude product was filtered with suction to remove the sodium chloride and then fractionally distilled in vacuo. At 48°–49° C. under 0.1 mm pressure, 32 g (75%) of colorless liquid 7-octenyl trimethoxysilane was obtained as the main product. At 127°–128° C. under 0.1 mm., 6.5 g (15%) of slightly colored liquid bis-7-octenyl dimethoxy disiloxane was received as a by-product.

Analyses, Calcd. for the trimethoxysilane, $C_{11}H_{24}SiO_3$: C, 56.85; H, 10.41. Found: C, 55.72; H, 9.53. Calcd. for the disiloxanes $C_{20}H_{44}Si_2O_5$: C, 57.09; H, 10.54. Found: C, 56.04; H, 9.87.

Both distillate products exhibited nmr spectra in accordance with their assumed structures.

B. Synthesis of Silylalkyl Phosphines

Example 6 — Addition of Diphenyl Phosphine to Vinyl Trichlorosilane

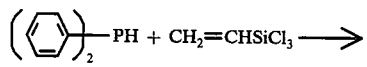

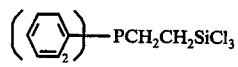

Into a quartz reaction vessel, equipped with a magnetic stirrer, nitrogen bubbler and a dropping funnel, was placed 13 g (0.07 mole) of the diphenyl phosphine reactant. To the stirred irradiated diphenyl phosphine under nitrogen was added 11.3 g (0.07 mole) of vinyl trichlorosilane in 5 minutes. The irradiation of the stirred reaction mixture at 15° C., by 275 watt Hanau immersion lamps having a high pressure mercury arc emitting a wide spectrum of irradiation, was continued for 24 hours. A subsequent analysis by nuclear magnetic resonance (nmr) spectroscopy of a sample indicated that an essentially quantitative addition reaction took place. No vinylic unsaturation was present in the final reaction mixture. The crude product was distilled in high vacuo to yield 19 g (80%) of distilled colorless liquid adduct boiling at 142°–144° C. at 0.1 mm. For elemental analyses see Table IV.

Example 7 — Addition of Phenyl Phosphine to Vinyl Trichlorosilane

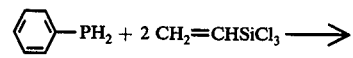

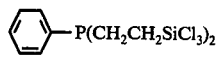

In the manner described in the previous example, 22 g. (0.2 mole) of phenyl phosphine was added to 64.6 g (0.4 mole) of vinyl trichlorosilane. Nmr spectroscopy of the crude adduct indicated the absence of olefinic unsaturation. Fractional distillation in vacuo yielded 73 g (85%) of the clear, colorless liquid adduct boiling between 131°–132° C. at 0.05 mm pressure.

Example 8 — Addition of Dihydrocarbyl Phosphines to ω-Alkenyl Silanes

In a manner described in Example 6, a number of secondary aromatic and aliphatic phosphines were added to the ω-alkenyl silanes described in Examples 1 to 5. The results of these addition experiments are summarized in Table IV.

In general, equimolar reactants were used. However, it was found that the alkenyl silane conversion could be raised when twofold amounts of the phosphine reactant were used.

The addition of phosphines to allyl and higher alkenyl silanes is proceeding at rates slower than to those to vinyl silanes (Table IV, Ref. Nos. 1-3 vs. 4-9). Addition to allyl trichlorosilane seems to occur with allylic reversal as a side reaction.

The addition of diphenyl phosphine to the olefinic unsaturation of the silanes occurs more readily than that of the more basic dialkyl phosphines (Table IV, Ref. Nos. 1, 7 vs. 2, 3, 8). The reduced reaction rate of the latter type of compounds is probably due to the increased donor interaction of their phosphorus atoms with the silicon.

These additions have a sharply reduced rate when internal alkenyl silanes are used in place of the ω-alkenyl compounds. The big rate difference suggests that steric crowding is an important factor in limiting the addition of bulky phosphinyl radicals to internal double bonds.

The silylalkylphosphine adducts were, in general, colorless, highly viscous liquids. Their high viscosity at room temperature is probably an indication of their high degree of molecular association due to $P \rightarrow Si$ interactions. They could be isolated by fractional distillation in high vacuo. Some of them were distilled at temperatures in excess of 200° C. without decomposition (Table IV, Ref. Nos. 5-10). This indicated that they possess a considerable thermal stability. The assumed structure of the adducts is supported by their elemental composition (Table IV). The non-branched polymethylene character of the alkylene groups bridging the phosphine and silane moieties is indicated by nmr.

TABLE IV
ω-SUBSTITUTED SILYLALYKYL PHOSPHINES VIA PHOSPHINE ADDITION TO ω-ALKENYL SILANES

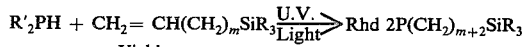

$$R'_2PH + CH_2=CH(CH_2)_mSiR_3 \xrightarrow[\text{Light}]{\text{U.V.}} Rhd\ 2P(CH_2)_{m+2}SiR_3$$

| Ref. No. | Chemical Structure | Yield, % (After Hrs.) | Boiling Range °C./mm | Calcd. C | Calcd. H | Calcd. P | Calcd. Cl | Found C | Found H | Found P | Found Cl |
|---|---|---|---|---|---|---|---|---|---|---|---|
| 1 | $(C_6H_5)_2P(CH_2)_2SiCl_3$ | 80(24) | 142–144/0.1 | 48.37 | 3.98 | | | 48.19 | 3.98 | | |
| 2 | $(C_6H_{11})_2P(CH_2)_2SiCl_3$ | 33(72) | 96–98/0.15 | 46.74 | 7.28 | | 29.57 | 45.84 | 6.88 | | 30.42 |
| 3 | $(C_3H_7)_2P(CH_2)_2SiCl_3$ | 50(24) | 77–78/0.5 | 34.36 | 6.49 | 11.08 | | 33.48 | 6.2 | 11.44 | |
| 4 | $(C_6H_5)_2P(CH_2)_2SiCl_3$ | 38(96) | 144–145/0.1 | 49.81 | 4.46 | 8.56 | 29.41 | 48.95 | 4.65 | 8.42 | 28.55 |
| 5 | $(C_6H_5)_2P(CH_2)_8SiCl_3$ | 70(37) | 218–221/0.5 | 55.63 | 6.06 | 7.17 | 24.64 | 55.64 | 5.92 | 7.78 | 23.29 |
| 6 | $(C_6H_5)_2P(CH_2)_8Si(CH_3)Cl_2$ | 34(96) | 188–189/0.1 | 61.31 | 7.10 | 7.53 | 17.24 | 60.45 | 6.60 | 7.84 | 16.30 |
| 7 | $(C_6H_5)_2P(CH_2)_8Si(OC_2H_5)_3$ | 46(72)** | 198–200/0.13 | 67.79 | 8.97 | | | 68.28 | 8.61 | | |
| 8 | $(C_6H_{11})_2P(CH_2)_8Si(OC_3H_5)_3$ | 26(72) | 195–197/0.1 | 66.06 | 11.30 | | | 6.04 | 10.50 | | |
| 9 | $(C_6H_5)_2P(CH_2)_{14}SiCl_3$ | 32(113)** | 188–190/0.05 | 60.52 | 7.42 | 6.00 | | 60.56 | 7.21 | 6.50 | |
| 10 | $(C_6H_5)_2P(CH_2)_2$—⟨ ⟩—$(CH_2)_2SiCl_3$ | 82(72)** | 200–225/0.3 | 58.48 | 4.91 | 6.86 | 23.54 | 60.09 | 5.12 | 7.07 | 22.53 |

\* Irradiation by ultraviolet light.
\*\* Two moles of phosphine per alkenyl silane were used.

Example 9 — Addition of Diphenyl Phosphine to 7-Octenyl Dimethoxychlorosilane

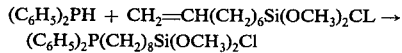

$(C_6H_5)_2PH + CH_2=CH(CH_2)_6Si(OCH_3)_2CL \rightarrow$
$(C_6H_5)_2P(CH_2)_8Si(OCH_3)_2Cl$ A mixture of 40.7 g (0.2 mole) diphenyl phosphine and 23.24 g (0.1 mole) 7-octenyl dimethoxy chlorosilane of Example 4 was irradiated at 15° for 72 hours. An nmr spectrum of the resulting liquid product showed the disappearance of most of the vinylic protons, indicating addition to form 8-dimethoxychlorosilyloctyl diphenyl phosphine. However, the product decomposed on attempted distillation in vacuo when heated to 210° C.

C. Anchoring to Silica

Example 10 — Dehydration of Silica Used for Anchoring

Grade HSF cab-o-sil, having a surface area about 300 M²/g, obtained from the Cabot Co., Boston, Mass., was heat-treated using a fluidized sand bath equipped with high vacuum stopcock and O-ring construction for 16 hours at >325° C. at $10^{-4}$ mm Hg vacuum pressure. According to the literature (see Advances in Catalysis and Related Subjects, Vol. 16, Ed. D. D. Eley, H. Pines, and P. B. Weise, H. P. Boehm, particularly pages 242–244, Acad. Press., New York, 1966), the above heat treatment of silica is sufficient to remove physically absorbed water. According to the above-referred literature the heat treated cab-o-sil so obtained has about 3 silanol groups per $10^{-6}$ cm² silica surface. One g cab-o-sil has $3 \times 10^6$ cm² surface which means $1.5 \times 10^{-3}$ mole equivalents of silanol. The above treated cab-o-sil was then transferred to a dry box and stored in a tightly capped bottle until use.

Example 11 — Reaction of the Phosphine $(C_6H_{11})_2P(CH_2)_2SiCl_3$ with Dehydrated Cab-o-sil A 1.87 g portion of $(C_6H_{11})_2P(CH_2)_2SiCl_3$ (5.0 mm) was dissolved in 40 ml benzene and added to 12.5 g dehydrated cab-o-sil of Example 10 in 5 ml portions with thorough grinding. The benzene was removed from the cab-o-sil by vacuum drying at $5 \times 10^{-2}$ mm Hg vacuum pressure for three hours at room temperature. The impregnated cab-o-sil was then heated at 100° C. at $5 \times 10^{-2}$ mm Hg pressure for sixteen hours. A sample of the phosphine on cab-o-sil was submitted for C, H, P, Cl analysis. Found: C, 6.85; H, 1.16; P, 1.10; Cl, 1.51. Calculated (assuming the phosphine $(C_6H_{11})_2P(CH_2)_2$ SiCl_3 was unreacted on the cab-o-sil surface): C, 6.07; H, 0.95; P, 1.12; Cl, 3.84. All operations involving air sensitive materials were performed in a nitrogen purged dry box. This example demonstrates that the above heat-treatment of this phosphine, on dehydrated cab-o-sil will eliminate 1.81 moles hydrogen chloride per mole phosphine from the cab-o-sil surface.

Example 12 — Reaction of The Anchored Phosphine of Example 11 With Rhodium Carbonyl Chloride A 5.76 g portion of the anchored phosphine, Example 11 containing 2.0 mm of phosphine, was impregnated with the light yellow solution of 0.194 g. $[(CO)_2RhCl]_2$ (0.50 mm) dissolved in 15 ml benzene. The impregnated complex was ground for 20 minutes to insure a homogeneous distribution of rhodium carbonyl chloride on the cab-o-sil surface. Following thorough mixing, the impregnated cab-o-sil was dried at ambient temperature for 1 hour at $5 \times 10^{-2}$ mm Hg vacuum pressure. Sixty ml of benzene was then added and the mixture was stirred for 10 minutes. The mixture was then suction filtered through a fine glass filter frit. Complete retention of the rhodium complex $[(C_6H_{11})_2P(CH_2)_2SiCl_3]_2Rh(CO)Cl$, on the cab-o-sil surface, was evidenced by the water white color of the benzene filtrate. The impregnated rhodium complex was then dried for 16 hours at $10^{-2}$ mm Hg vacuum pressure at 50° C. A sample of the anchored rhodium complex was submitted for C, H, Rh, P, Cl analyses. Found: C, 6.84; H, 1.26; Rh, 1.86; P, 1.06; Cl, 1.42; Calculated (assuming the complex $[C_6H_{11})_2P(CH_2)_2SiCl_3]_2$ Rh(CO)Cl was the product of the above reaction); C, 6.36; H, 0.96; Rh, 1.88; P, 1.13; Cl, 4.53.

This example demonstrates the ready formation of an anchored phosphine-rhodium complex by impregnation of rhodium dicarbonyl chloride dimer onto phosphine anchored to cab-o-sil below its point of incipient wetness.

Example 13 — Anchoring of Various Silylalkyl Phosphines and Their Transition Metal Complexes In a series of experiments the dehydrated silica of Example 10 was reacted with about $0.2 \times 10^{-3}$ mole of a trichlorosilylalkyl phosphine or its transition metal complex per g silica. In general, the novel anchored complexes were prepared in benzene, which is a good solvent for both the free and complexed phosphines.

In most cases, the complexing of silylalkyl phosphines was effected after anchoring to silica. The occurrence of complexing was then established by analyzing the modified silica for metal as well as phosphorus content. As indicated by the data of Table V, the found and calculated phosphorus contents are in good agreement. In general, the transition metal compound reactants were employed in stoichiometric amounts in benzene solutions. Quantitative reaction with the anchored phosphine complexes was indicated by the absence of the color of the metal complex from the benzene after treatment. The structure of all the complexes containing a carbonyl group remained unchanged; as indicated by a single strong carbonyl stretching frequency in the 1960–1990 cm$^{-1}$ region of the infrared spectra of the complexes follow exposure to a carbon monoxide atmosphere.

Typical methods of anchored silylalkyl phosphine-rhodium complex preparation, referred to in Table V, are outlined below:

A. About 4% benzene solution of $2m$ mole silylalkyl phosphine-rhodium complex was added to 10 g dehydrated cab-o-sil with thorough grinding to effect impregnation Benzene was then removed at a pressure of 0.05mm and hydrogen chloride eliminated by heating at 140° C. for 14 hours.

B. On about 5.7 g sample of modified methanol treated cab-o-sil having $2m$ mole of anchored silylalkyl phosphine was impregnated with a 20 ml benzene solution of $0.5m$ mole of rhodium compound. The benzene was then removed in vacuo and the dried product washed with 60 ml benzene, filtered with suction and dried at 50° C. for 3 hours at 0.05 mm pressure.

C. A procedure similar to B was followed starting with cab-o-sil not subsequently exposed to methanol.

D. A procedure similar to B was followed, but the washing with benzene omitted.

E. A procedure similar to A was followed plus the product was treated with excess methanol at ambient temperature.

In general, at least one mole of hydrochloric acid per mole phosphine was eliminated presumably by the following anchoring reaction:

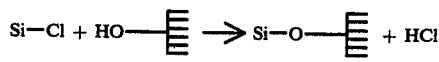

The degree of this type of reaction was reflected in the

Table V

Preparation of Rhodium Complexes of 3-(Trichlorosilyl)-alkyl Phosphines Anchored to Silica Via the Reaction $$R_2'P(CH_2)_nSiCl_3 + HOSi(SiO_2)_n \longrightarrow R_3'P(CH_2)_nSiCl_2-OSi(SiO_2)_n \text{ etc.}$$

| Seq. No. | Form of Phosphine Anchoring Reagent | Rhodium Compound Reagent | Rhodium Compound - Anchored Phosphine Complex Disregarding HCl Elimination on Anchoring to Silica Chemical Structure | Calculated Composition, % | | | | Method of Preparation | Found Composition, % | | | | |
|---|---|---|---|---|---|---|---|---|---|---|---|---|---|
| | | | | C | H | Rh | P | Cl | | C | H | Me | P | Cl |
| 1 | Complex | $Rh(CO)_2Cl_2$ | $[(C_6H_5)_2P(CH_2)_2SiCl_3]_2Rh(CO)Cl$ | 5.99 | 0.48 | 1.77 | 1.07 | 4.27 | A | 6.44 | 0.88 | 1.53 | 0.90 | 2.53 |
| 2 | Free | | | | | | | | B(CH$_3$OH) | 7.25 | 0.93 | 1.65 | 1.12 | 1.48 |
| 3 | Free | | $[(C_6H_{11})_2P(CH_2)_2SiCl_3]_2Rh(CO)Cl$ | 6.36 | 0.96 | 1.88 | 1.13 | 4.53 | C | 6.84 | 1.26 | 1.86 | 1.06 | 1.42 |
| 4 | Free | | $[(C_6H_5)_2P(CH_2)_8SiCl_3]_2Rh(CO)Cl$ | 8.17 | 0.87 | 1.71 | 1.03 | 4.11 | D(CH$_3$OH) | 9.18 | 1.16 | 1.70 | 1.02 | 0.70 |
| 5 | Free | [Rh(1,5-COD)Cl]$_2$ | $[(C_6H_{11})_2P(CH_2)_2SiCl_3]_2RhCl$ | 5.77 | 0.48 | 1.18 | 1.06 | 4.06 | B | 7.88 | 1.01 | 1.77 | 1.08 | 1.08 |
| 6 | Free | | $[(C_6H_5)_2P(CH_2)_2SiCl_3]_2RhCl$ | 6.36 | 0.98 | 1.29 | 1.16 | 4.44 | C | 7.36 | 1.52 | — | 1.03 | 2.02 |
| 7 | Free | | $[(C_6H_5)_2P(CH_2)_8SiCl_3]_2RhCl$ | 8.04 | 0.88 | 1.15 | 1.07 | 3.96 | B | 9.07 | 1.18 | 1.16 | 1.09 | 0.60 |
| 8 | Complex | | $(C_6H_5)_2P(CH_2)_2SiCl_3Rh(1,5-COD)Cl$ | 8.54 | 0.85 | | | | E(CH$_3$OH) | 6.03 | 0.74 | 1.28 | | |
| 9 | Complex | | $(C_6H_5)_2P(CH_2)_2Si(OC_2H_5)_3Rh(1,5-COD)Cl$ | 9.86 | 1.22 | | | | | 5.24 | 0.76 | | | |
| 10 | Complex | | $(C_6H_5)_2P(CH_2)_8SiCl_3Rh(1,5-COD)Cl$ | 10.6 | 1.20 | 3.23 | 0.97 | 4.45 | A | 10.31 | 1.34 | 3.44 | 1.15 | 3.57 |
| 11 | Complex | | $(C_6H_5)_2P(CH_2)_{14}SiCl_3Rh(1,5-COD)Cl$ | 12.51 | 1.54 | | | | E(CH$_3$OH) | 7.48 | 1.35 | | | |

Table VI

Preparation of Palladium and Cobalt Complexes of 8-(Trichlorosilyl)-octyl Phosphine and 2-(Trichlorosilyl)-ethyl Diphenyl Phosphine Anchored to Silica

| Seq. No. | Transition Compound Reagent | Transition Metal-Anchored Phosphine Complex Disregarding HCl Elimination on Anchoring to Silica Chemical Structure | Calculated Composition, % C | H | Me | P | Cl | Method of Preparation | Found Composition, % C | H | M | P | Cl |
|---|---|---|---|---|---|---|---|---|---|---|---|---|---|
| 1 | Pd(AcAc)$_2$* | $(C_6H_5)_2P(CH_2)_8SiCl_3Pd(AcAc)_2$ | 11.31 | 1.26 | 3.34 | 0.97 | 3.34 | B (CH$_3$OH) | 10.37 | 1.34 | 2.35 | 1.02 | 1.51 |
| 2 | $(C_6H_5CN)_2PdCl_2$ | $[(C_6H_5)_2P(CH_2)_8SiCl_3]_2PdCl_2$ | 7.95 | 0.87 | 1.76 | 1.02 | 4.69 | A | 8.47 | 0.72 | 1.73 | 1.08 | 1.84 |
| 3 | | $(C_6H_5)_2P(CH_2)_8SiCl_3Pd(C_6H_5CN)Cl_2$ | 5.68 | 0.55 | 1.86 | 0.54 | 3.10 | A | 7.43 | 1.05 | 1.73 | 0.86 | 2.39 |
| 4 | Co(CO)$_8$ | $[(C_6H_5)_2P(CH_2)_2SiCl_3]_2Co(CO)_6$ | | | 5.97 | 3.08 | 10.8 | A** | | | 6.85 | 2.18 | 11.1 |
| 5 | Co(CH$_3$)(CO)$_4$ | $(C_6H_5)_2P(CH_2)_2SiCl_3Co(CO)CH_3$-(10)$_3$ | 4.14 | 0.31 | 1.07 | 0.56 | 1.92 | A | 3.42 | 0.62 | 0.84 | 0.38 | 2.30 |

* Palladium bisacetyl acetonate.
**The complex (4.9 g, 5m mole) was dissolved in a minimum volume of benzene, and the solution added to 5g cab-o-sil with thorough mixing. The mixture was then evacuated and heated at 140° C. for 2 hours at 0.05mm to remove the solvent and the hydrogen chloride formed.

Table VII

Anchoring Reactions of 2-(Trichlorosilyl)-ethyl Diphenyl Phosphine with Silica and Subsequent Reactions with Methanol of the Resulting Anchored Phosphine

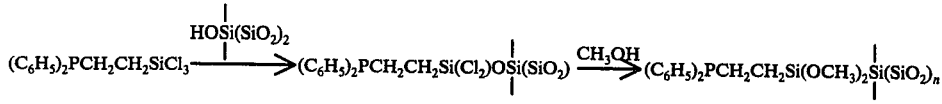

| Seq. No. | Phosphine, m mole per g silica | Reaction Conditions (Sequential) In Benzene °C. | hrs. | After Drying °C. | hrs. | mm | After Treatment Soxiet Extraction Solvent (Reagent) | Found Composition, % (Calcd. for Reactant Mixture) C | H | P | Cl |
|---|---|---|---|---|---|---|---|---|---|---|---|
| 1 | 1.6 (dehydrated) | 25 | <3 | 155 | 18 | 0.05 | | (17.58) | (1.48) | (3.24) | (11.12) |
| | | | | | | | | 20.16 | 1.77 | 3.60 | 7.49 |
| | | | | | | | Dry Benzene | 12.92 | 1.40 | 2.16 | 3.82 |
| | | | | | | | Wet Benzene | 13.03 | 1.30 | 1.92 | 1.69 |
| | | | | | | | Methanol, then Pyridine/Benzene | 13.55 | 1.35 | 1.92 | 0.97 |
| 2 | 6 (hydrated) | 80 | 4 | 25 | 2 | 0.05 | | (32.69) | (2.74) | (6.02) | (20.6) |
| | | | | | | | | 13.35 | 1.35 | 2.21 | 2.39 |
| | | | | | | | Dry Benzene | 12.27 | 1.17 | 2.22 | 1.66 |
| 3 | 0.4 (dehydrated) | 25 | 2 | | | | | (5.90) | (0.50) | (1.09) | (3.73) |
| | | | | | | | | 7.19 | 0.87 | 1.15 | 2.18 |
| | | | | | | | Methanol | 7.12 | 0.83 | 1.14 | 1.03 | chlorine content of the anchored phosphine (Tables V and VI). The phosphorus content was generally about 1%.

Example 14 — Stability of Anchored Trichlorosilylated Phosphines

The anchoring of 2-(trichlorosilyl)-ethyl diphenyl phosphine and the stability and reactivity of the resulting anchored phosphine was studied in some detail. The results are summarized in Table VII. The data show that using an excess of the phosphine, about 1m mole phosphine can be anchored to 1g silica, i.e., to a surface of $3 \times 10^6$ cm$^2$. Anchoring, involving one chlorine of the silyl group, occurs even at room temperature to either the dehydrated or hydrated silica. The anchored phosphine is stable to extraction by either benzene or methanol. However, methanol or water does react with the chlorosilyl groups as indicated by the decreased chlorine contents. About one chlorine per phosphorus atom still remained in the anchored composition. It is felt, however, that this chlorine may have migrated from the original silicon atom it was attached via reversible chlorosilane hydrolysis. Any hydrogen chloride formed will also complex reversibly with the phosphine groups.

As a result of water or methanol treatment, some of the chlorosilane groups are converted to silanol groups. These in turn might undergo siloxane condensation.

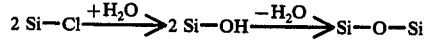

Example 15 — Anchoring a Phosphine at Room Temperature and its Subsequent Reaction with Methanol A 4.33 g portion of $\phi_2P(CH_2)_8SiCl_3$ (10.0 mm) was impregnated onto 25 g dehydrated cab-o-sil utilized two impregnations of 4 mm of $\phi_2P(CH_2)_8SiCl_3$ dissolved in 40 ml benzene onto two-10 g portions of dehydrated cab-o-sil, and one impregnation of 2 mm of $\phi_2P(CH_2)_8SiCl_3$ dissolved in 20 ml benzene onto one 5 g portion of dehydrated cab-o-sil. The three portions were combined in a 1000 cc side arm vacuum flask and dried for three hours at ambient temperature at $5 \times 10^{-2}$ mm Hg vacuum pressure. A 300 ml portion of methanol was added to the impregnated phosphine and the mixture was refluxed with stirring for 2 hours. The mixture was then vacuum filtered through a fine glass filter frit and the residue was washed with two 50 ml portions methanol. The residue was dried for 16 hours at 80° C. at $5 \times 10^{-2}$ mm Hg vacuum pressure. A portion of the methanol washed sample was submitted for C, H, P, Cl analysis: Found: C, 9.12; H, 1.18; P, 1.04; Cl, 0.21; Calculated (assuming the phosphine $\phi P(CH_2)_8SiCl_3$ was unreacted on the cab-o-sil surface) C, 8.19; H, 0.89; P, 1.06; Cl, 3.63. This example again demonstrates the reaction of a trichlorosilylated phosphine with dehydrated cab-o-sil at ambient temperature.

This example also demonstrates that the chlorosilyl groups have increased reactivity towards methanol if they are separated from the phosphine group by a polymethylene chain.

D. Catalysis Using Anchored Phosphine - Metal Complexes

Example 16 — Anchored Catalysts of Propylene Hydroformylation and Cyclohexene Hydrogenation Propylene hydroformylation catalytic activity of the heterogeneous rhodium catalysts of Example 13, Table V, Sequence Nos. 3, 6, 2, 5, 4, 7, 10, 8, 11, 9 were impregnated in an Autoclave Engineer's 300 cc capacity autoclave. The heterogeneous rhodium catalysts were placed in a glass liner to which 70 ml benzene had been added. All operations were performed in a nitrogen purged dry box. The glass liner was sealed with a rubber stopper and transferred to the autoclave where the glass liner was blanked by a purge of argon during assemblage of the autoclave stirrer. Propylene was introduced to the stirred benzene solution until the benzene solution was saturated. The propylene concentration was found to be reasonably constant by the above procedure. The temperature was increased to 100° C. and $CO/H_2$ (50:50 blend) was added to give a total pressure of 1000 psi. The temperature was increased slowly up to a maximum temperature of 180° C. The total $CO/H_2$ absorbed was noted as well as the time and temperature at each increment.

Propylene was hydroformylated to form mainly butyraldehyde in a saturated benzene solution. The activity of the various catalysts studied was observed at the 0.1–0.5m mole level as a function of $CO/H_2$ absorbed. During the experiment the temperature of the mixture was increased to either a maximum of 180° C. or to the temperature of virtually complete conversion. While the reaction was in progress, the pressure drop from 1000 psi was recorded and the pressure readjusted repeatedly. The relative rate of the reaction was semi-quantitatively determined by summing up the pressure drop during the period of observation. The greater the pressure drop and the lower the temperature and the shorter the reaction time are, the higher the reaction rate is with a certain catalyst.

In the cyclohexene hydrogenation studies, a 1M benzene solution was used with a catalyst containing 2.5m mole rhodium. At a constant, 50 psig pressure of hydrogen, the temperature necessary to reach a 1 psig per minute hydrogen uptake was determined for each catalyst.

The results of both hydroformylation and hydrogenation studies are shown by Table VIII. They indicate that several of the anchored catalysts have activities comparable to homogeneous catalysts of similar structure. Most interestingly the results also show that the activities are dependent on the length of the alkylene chain linking the phosphine ligand to the silica. Furthermore, the effect of the alkylene chain on the catalytic activity is dependent on the method of anchoring and on the reaction being examined. Both the kind of reactive anchoring groups and the length of the alkylene group have a profound effect on hydroformylation but no significant effect on hydrogenation activity.

In the hydroformylation reaction, the catalysts derived by complexing anchored 2-(trichlorosilyl)-ethyl phosphines, i.e., trichlorosilyl phosphines having a two carbon alkylene chain (Sequence Nos. 1, 2, 5, 7, 9), are completely inactive. In contrast, analogous 2-(triethoxysilyl)-ethyl phosphine derived catalysts (Sequence Nos. 6, 10) are very active. Also in contrast, the use of anchored-(trichlorosilyl)-alkyl phosphines having longer alkylene chains, i.e., octamethylene or tetradecamethylene groups (Sequence Nos. 3, 4, 8, 11, 12) led to very active rhodium catalysts.

A comparison of the hydroformylation catalysts derived from 8-(trichlorosilyl)-octyl diphenyl phosphine (Ref. Nos. 3, 6, 8, 11) indicate that the degree of activity is directly proportional with the phosphine coordination number at the metal center. For example, the L Rh (1,5-COD)Cl complex (No. 11) is much more active than the $L_3RhCl$ complex (No. 8).

In the hydrogenation reaction, the structure of the anchoring reagent has little, if any, effect. With the exception of the anchored complexes having a carbonyl ligand (Ref. Nos. 1–3), all the compositions were active. In contrast to the hydroformylation, hydrogenation rates were increased with increasing phosphine coordination number at the metal center. For example, the L Rh(1,5-COD)Cl complexes (Nos. 9 and 11) are less active hydrogenation catalysts than the corresponding $L_3RhCl$ complexes (Nos. 5 and 8).

It was interesting to compare the catalytic activity of anchored complex catalysts and soluble complex catalysts of similar structure. It was found that the activity of the best anchored catalysts for hydroformylation (Nos. 10–12) and hydrogenation (Nos. 5 and 8) is of the same order of magnitude as that of the soluble triphenylphosphine rhodium chloride (No. 13). However, it has to be pointed out that a direct comparison of activities is most difficult. The soluble catalyst complex (No. 13) has no activity whatsoever in the presence of cab-o-sil. The hydroxyl groups of silica apparently completely inhibit its catalytic activity.

Table VIII

Propylene Hydroformylation and Cyclohexene Hydrogenation with Anchored Silylalkyl Phoshine-Rhodium Complex Catalysts

| Seq. No. | Rhodium Compound-Anchored Phosphine Complex Disregarding HCl Elimination on Anchoring | Seq. No. in Ex.13 | Rhodium Catalyst m mole | Hydroformylaton Reactants (CO/H₂) Consumed, psi drop | Reaction Conditions Temperature Range, °C | Time Min. | Activity Estimate Hydro-formulation | Activity Estimate Hydrogena-tion | Hydrogenation Temperature Cat. 1 psig per min. H₂ uptake | C-173 Ref. No. |
|---|---|---|---|---|---|---|---|---|---|---|
| 1 | [(C₆H₅)₂P(CH₂)₂SiCl₂]₂Rh(CO)Cl | 1 | 0.5 | 0 | 100–160 | 72 | None | None | — | — |
| 2 | [(C₆H₁₁)₂P(CH₂)₂SiCl₂]₂Rh(CO)Cl | 3 | 0.5 | 0 | 100–180 | 77 | None | — | — | — |
| 3 | [(C₆H₁₁)₂P(CH₂)₈SiCl₂]₂Rh(CO)Cl | 4 | 0.1 | 115 | 100–175 | 118 | Moderate | None | — | — |
| 4 | [(C₆H₅)₃P(CH₂)₂SiCl₃]₂RhCl₂ | | | | | | | Moderate | 95 | 63 |
| 5 | (C₆H₅)₂P(CH₂)₂Si(OC₂H₅)₃RhCl | 5 | 0.4 | 0 | 100–155 | 83 | None | High | 70 | — |
| 6 | (C₆H₁₁)₂P(CH₂)₂SiCl₃RhCl | | 0.5 | 1100 | 100–175 | 134 | Moderate | — | — | — |
| 7 | (C₆H₅)₂P(CH₂)₈SiCl₃RhCl | 6 | 0.3 | 0 | 100–165 | 143 | None | High | 70 | 59 |
| 8 | (C₆H₅)₂P(CH₂)₂SiCl₃Rh(1,5-COD)Cl | 7 | 0.1 | 195 | 100–145 | 151 | Moderate | Moderate | 80 | 65 |
| 9 | (C₆H₅)₂P(CH₂)₂Si(OC₆H₅)₂Ph(1,5-COD)Cl | 8 | 0.5 | 0 | 100–175 | 75 | None | — | — | — |
| 10 | (C₆H₅)₂P(CH₂)₈SiCl₃Rh(1,5-COD)Cl | 9 | 0.5 | 1070 | 100–150 | 149 | High | Moderate | 90 | 58 |
| 11 | (C₆H₅)₂P(CH₂)₂₈SiCl₃Rh(1,5-COD)Cl | 10 | 0.5 | 1160 | 100–140 | 176 | High | — | — | — |
| 12 | (C₆H₅)₂P(CH₂)₁₄SiCl₃Rh(1,5-COD)Cl | 11 | 0.5 | 1160 | 100–150 | 154 | High | High | 55 | 66 |
| 13 | [(C₆H₅)₃P]₃RhCl | 4 | 1 | 780 | 150 | 25 | High | High | 75 | 70 |
| 14 | [Rh(1,3-COD)Cl]₂ | | | — | — | — | — | — | — | — |

Hydrogenation of cyclohexene was investigated for a number of anchored rhodium phosphine complexes of the formula $L_xRhCl$, where $x = 1, 2, 3$ and where L is a trichlorosilylated phosphine chemically affixed to cab-o-sil, in order to establish the sensitivity of the hydrogenation reaction rate to coordination number about the metal and to the type of phosphine. The active homogeneous hydrogenation catalyst $(\phi_3P)_3RhCl$ was used as comparison to the anchored rhodium phosphine catalysts investigated. Standard cyclohexene hydrogenation conditions were determined by investigating the activity of 0.125 mm $(\phi_3P)_3RhCl$ catalyst in 50 ml of 1M solution of cyclohexene (dried over sodium metal and stored under nitrogen in benzene. The catalyst concentration was 2.5 mM in rhodium catalyst. All hydrogenation reactions were investigated at a constant hydrogen pressure of 50 psig. The temperature of hydrogen uptake of about 1 psig per minute was determined for each catalyst. All of the hydrogenation reactions were investigated using a 300 cc capacity Fisher high pressure reaction bottle equipped with pressure gauge and gas inlet and outlet valves.

Example 17 — Activity Maintenance of Anchored rhodium phosphine complex in Propylene Hydroformylation Because of the marked greater activity of catalyst No. 11 of Table VIII a number of recycling steps with the catalyst were performed and demonstrated an increase in catalytic activity with no apparent decrease beyond a consistently high activity. A 0.5 mm, as rhodium, gave a total of 420 pounds $CO/H_2$ uptake over a 210 minute interval with a final temperature of 175° C. The catalyst from the above hydroformylation run was suction filtered through a fine sintered glass frit. The residue was washed with 100 ml benzene. Before the rhodium complex on cab-o-sil was allowed to dry, the catalyst was recharged for another hydroformylation run. The catalyst was carried out over a time interval of 86 minutes at 135° C. with a total $CO/H_2$ consumption of 1320 pounds. The catalyst was filtered, washed with 100 ml benzene and recharged as previously described above. The catalysis was carried out over a time interval of 175 min. at 135° C. with a total $CO/H_2$ consumption of 1160 pounds. Normal butyraldehyde to iso-butyraldehyde ratio was 1.05 and 1.25 for the latter two runs, respectively. Similar effectiveness is observed for an analogous homogeneous triphenylphosphine complex catalyst. This example demonstrates that the anchored rhodium-phosphine catalysts are effective for hydroformylation and retain their activity through several cycles.

Example 18 — Maintenance of Cyclohexene Hydrogenation activity of the anchored rhodium phosphine complex where Rh: P ratio is 1:1.

The catalyst benzene mixture was clear and light yellow in color. A reaction rate of 1 psig $H_2$/min. was observed at 115° C. The reaction mixture was taken into a nitrogen purged dry box and suction filtered with a fine sintered glass filter frit. The residue was washed with 100 ml benzene and recharged for another hydrogenation run. The reaction solution was clear and light grey in color. The hydrogenation rate of the recycled catalyst was the same as the initial hydrogenation rate. The reaction mixture was taken into a nitrogen purged dry box and suction filtered through a fine sintered glass filter frit. The residue was washed with 100 ml benzene and recharged for another hydrogenation run following exposure of the reaction mixture to 50 psi carbon monoxide for fifteen minutes with vigorous stirring. The carbon monoxide was vented and the reactor was repressured with 50 psig $H_2$. The exposure of the hydrogenation catalyst to carbon monoxide completely inhibited catalytic hydrogenation activity of cyclohexene up to a temperature of 157° C.

This example demonstrates that the anchored rhodium phosphine complex with Rh:P ratio of 1:1 can be repeatedly recycled without decrease in catalytic dehydrogenation activity. This example also demonstrates the poisoning effect of carbon monoxide on the catalytic hydrogenation activity of the anchored rhodium catalyst. Carbon monoxide poisoning was also observed for rhodium black and $(\phi_3P)_3RhCl$. This example provides a comparison between the catalytic hydrogenation activity of the above anchored catalyst with a Rh:P ratio of 1:1 and the anchored catalyst with a Rh:P ratio of 1:3. The catalytic hydrogenation activity is greater for the latter catalyst. This example also provides a comparison between the catalytic hydrogenation activity of anchored rhodium catalysts prepared by different techniques. The in situ preparation of the anchored rhodium catalyst with a Rh:P ratio of 1:1 is significantly more active.

Example 19 — Hydrogenation of cyclohexene using 1,5-cyclooctadiene rhodium chloride dimer in the presence of dehydrated cab-o-sil.

The homogeneous hydrogenation catalyst 1,5-cyclooctadiene rhodium chloride dimer exhibited a reaction rate of 0.365 psig $H_2$/min. at 100° C. The mixture was a grey color at this temperature. The reaction was stopped after a total hydrogen consumption of 13 psig. The hydrogen was vented from the reactor and the reactor was pressured to 50 psig with carbon monoxide for 15 minutes with vigorous stirring of the reaction solution. The carbon monoxide was vented from the reactor and the reactor was pressured with 50 psig $H_2$. The homogeneous catalyst was inactive for cyclohexene hydrogenation up to a temperature of 100° C.

This example is provided only as a comparison to the anchored catalysts of the previous examples. This example demonstrates the significant reduction of the hydrogenation activity of 1,5-cyclooctadiene rhodium chloride dimer by dehydrated cab-o-sil. It also demonstrates the poisoning effect of carbon monoxide on the 1,5-cyclooctadiene rhodium chloride complex in the presence of cab-o-sil.

Example 20 — Methanol Carbonylation Using An Anchored Phosphine-Rhodium Complex (a) Preparation of $[(\phi_2P(CH_2)_2SiCl_3]_2Rh(CO)Cl$ Dichlorotetracarbonyl dirhodium, 2.80 g (7.2 mm), was dissolved in 50 ml of benzene. A 10 g portion of $\phi_2P(CH_2)_2SiCl_3$ (28.8 mm), dissolved in 50 ml benzene was added slowly with stirring to the dichlorotetracarbonyl dirhodium. Reaction was evidenced by the immediate color change on mixing the two solutions from orange to light yellow with rapid gas evolution from solution. After ten minutes of vigorous stirring, benzene was removed by vacuum drying (5 × $10^{-2}$ mm Hg). The residue, following vacuum drying, was washed with four-5 ml portion hexane to yield 12.40 grams of the expected yellow crystalline product, $[\phi_2P(CH_2)_2SiCl_3]_2Rh(CO)Cl$, in essentially 100% yield.

The yellow crystalline product had a melting point 168°-169° C., decomposing on melting to a deep red liquid. The complex [$\phi_2$P(CH$_2$)$_2$SiCl$_3$]$_2$Rh(CO)Cl exhibited a single strong carbonyl stretching frequency at 1977 cm$^{-1}$ compared to the ($\phi_3$P)$_2$Rh(CO)Cl carbonyl stretching frequency in benzene of 1975 cm$^{-1}$. The crystalline complex was submitted for C, H, Rh, P, Cl analysis, Found: C, 40.63; H, 3.25; Rh, 12.2; P, 6.94; Cl, 28.13; Calculated C$_{29}$H$_{28}$O,RhSi$_2$Cl$_2$P$_2$: C, 40.42; H, 3.28; Rh, 11.94; P, 7.19; Cl, 28.8.

This example demonstrates the ability to prepare and isolate an L$_2$Rh(CO)Cl complex where L is a trichlorosilyl group containing phosphine.

(b) Reaction of [$\phi_2$P(CH$_2$)$_2$SiCl$_3$]$_2$Rh(CO)Cl with dehydrated cab-o-sil.

A 1.72 g portion of [$\phi_2$P(CH$_2$)$_2$SiCl$_3$] Rh(CO)Cl (2.0 mm was dissolved in 40 cc benzene. The benzene solution was added dropwise to 10 g dehydrated cab-o-sil with thorough grinding. Benzene was removed from the rhodium complex impregnated onto cab-o-sil by vacuum drying at ambient temperature for 1 hr. at 5 × 10$^{-2}$ mm Hg vacuum pressure. The rhodium complex impregnated onto cab-o-sil was then heated at 140° C. for 14 hours at 5 × 10$^{-2}$ mm Hg vacuum pressure. The above heat treatment eliminated hydrogen chloride gas from reaction of the chlorosilane groups with the hydroxyl groups of the silica surface as analysis of the liquid nitrogen vacuum trap from the fourteen hour heat treatment gave acid concentration equivalent to 0.25 mm HCl per mm rhodium. Direct chemical analysis of the rhodium complex on cab-o-sil indicated 2.8 mm chlorine per mm rhodium had been removed from the cab-o-sil surface as hydrogen chloride, as shown by the following. Found: C, 6.44; H, 0.88; Rh, 1.53; P, 0.90; Cl, 2.53; calculated (determined on the assumption that the complex [$\phi_2$P(CH$_2$)$_2$SiCl$_3$]$_2$ Rh(CO)Cl was present on the cab-o-sil surface according to the concentration above, i.e., 2 mm rhodium complex/10 g cab-o-sil: C, 5.93; H, 0.48; Rh, 1.73; P, 1.06; Cl, 4.23.

The above example demonstrates again the facile reaction of a trichlorosilylated phosphine-rhodium complex with dehydrated cab-o-sil.

(c) The anchored phosphine rhodium complex as a methanol carbonylation catalyst.

A 2.95 g portion of [$\phi_2$P(CH$_2$)$_2$SiCl$_3$]$_2$Rh(CO)Cl/cab-o-sil (0.5 mm as rhodium), was placed in a glass liner of a 200 cc capacity Roth autoclave with 63 ml methanol and 7 ml benzene. Methyl iodide was used as a co-catalyst and 0.25 ml was added to the above mixture. The 200 cc capacity Roth autoclave was sealed in the dry box and transferred to the hood. Magnetic stirring was used during the course of the reaction. The Roth autoclave was then pressurized with CO at ambient temperature to 250 psi. The temperature was increased to 145° C. and maintained for 17 hours. Quantitative g.c. analysis of the distilled reaction solution gave the following wt. percent of components; H$_2$O, 5.0; CH$_3$OH, 75.7; CH$_3$CO(OCH$_3$), 10.5; C$_6$H$_6$, 8.8. Analysis of a portion of several catalysts following analogous methanol carbonylation run conditions using the above conditions and the same rhodium complex, demonstrate that the rhodium complex had remained affixed to the cab-o-sil surface under reaction conditions. Analysis of several spent methanol carbonylation runs with the above anchored catalyst is given to illustrate the ability of the anchored rhodium complex to function as a heterogeneous catalyst in slurry reactions without loss of the precious metal: Found: Spent catalyst from run #A: C, 6.28; H, 0.89; Rh, 1.59; P, 0.75: Cl, 0.63; spent catalyst run #C; C, 6.76; H, 0.84; Rh, 1.63; P, 0.95; Cl, 1.23 spent catalyst run #G; C, 6.63, H, 1.14, Rh, 2.02; P, 0.91; Cl, 1.15. The above elemental compositions compare well with that of the starting anchored catalyst except for the decreased chlorine values.

This example when compared with the following experiment demonstrates the near equivalent methaol carbonylation activity of the anchored rhodium complex compared to the analogous homogeneous catalyst ($\phi_3$P)$_2$Rh(CO)Cl. This example also demonstrates the retention of the rhodium metal on the cab-o-sil surface under methanol carbonylation reaction conditions.

(d) ($\phi_3$P)$_2$Rh(CO)Cl as a methanol carbonylation catalyst.

A 0.345 g amount of ($\phi_3$P)$_2$Rh(CO)Cl was placed in a glass liner for a 200 cc capacity Roth autoclave with 63 ml methanol/7 ml. benzene. Methyl iodide was used as a co-catalyst and 0.125 ml was added to the above mixture. The 200 cc capacity Roth autoclave was sealed in the dry box and transferred to the hood. Magnetic stirring was used during the course of the reaction. The autoclave was then pressurized with CO at ambient temperature to 250 psi. The temperature was increased to 175° C. and maintained for 20 hrs. Quantitative g.c. analysis of the distilled reaction solution gave the following weight percent of components: H$_2$O, 11.2; CH$_3$OH, 63.3; (CH$_3$)$_2$O, 3.8; CH$_3$CO(OCH$_3$), 11.1; CH$_3$COOH, 0.1; C$_6$H$_6$, 10.5.

This example is included only to provide a comparison of the activity of a homogeneous methanol carbonylation catalyst to the heterogeneous methanol carbonylation catalyst.

(e) Blank runs of the methanol carbonylation reactor.

(1) A 2.5 g amount of dehydrated cab-o-sil, was placed in a glass liner of a 200 cc capacity Roth autoclave with 45 ml methanol/7 ml benzene solution. Methyl iodide (0.5 ml) was added and the Roth autoclave was sealed in the dry box and transferred to the hood. The autoclave was pressured at ambient temperature to 250 psi CO at ambient temperature. Magnetic stirring was used during the course of the reaction. Gas chromatographic analysis showed no methyl acetate was produced for a run time of sixteen hours at 140° C. (2) A 0.25 ml portion of methyl iodide was placed in a 200 cc capacity Roth autoclave with 63 ml methanol/7 ml benzene. The Roth autoclave was sealed in the dry box and transferred to the hood. The autoclave was pressured to 250 psi CO at ambient temperature. The temperature was increased to 150° C. and maintained for sixteen hours. Quantitative g.c. analysis gave the following weight percent; H$_2$O, 6.1; (CH$_3$)$_2$O, 6.0; CH$_3$OH, 75.5; CH$_3$CO(OCH$_3$), 0.1; C$_6$H$_6$, 11.3.

This example is included only to provide a demonstration that cab-o-sil and methyl iodide, or methyl iodide in the absence of cab-o-sil are not catalytic for methanol carbonylation under the reaction conditions employed in (c) and (d) above.

(f) The anchored phosphine of (b) exposed to benzene Soxlet extraction and concentrated acetic acid at 150° C.

To establish that the anchored phosphine rhodium complex of (c) would remain intact as a heterogeneous phase in the presence of various liquid phases, the following experiments were executed: (1) A portion of the anchored phosphine rhodium complex of (c) was heated for two hours at 150° C. in 100 ml concentrated acetic acid in a 200 cc capacity Roth autoclave. The above acetic acid solution was suction filtered through a fine glass filter frit in a nitrogen purged dry box and washed with two-50 ml portion benzene. The residue was vacuum dried for 1 hour at ambient temperature at $5 \times 10^{-2}$ mm Hg vacuum. The dried anchored rhodium complex on cab-o-sil was submitted for C, H, Rh, P, Cl analysis. Found: C, 7.10; H, 0.93; Rh, 1.67; P, 0.95; Cl, 1.43; Calculated (as in (b)) C, 5.93; H, 0.48; Rh, 1.73; P, 1.03, Cl, 4.23. (2) A portion of the anchored phosphine rhodium complex of (b) was Soxlet extracted with benzene under a nitrogen purge for 19 hours. Following vacuum drying the rhodium complex on cab-o-sil was submitted for C, H, Rh, P, Cl analysis. Found: C, 5.97; H, 0.70; Rh, 1.70; P, 1.03; Cl, 1.47.

This example demonstrates the retention of the anchored phosphine complex on the cab-o-sil surface under continuous benzene refluxing and heating with concentrated acetic acid at 150° C.

Example 21 — Mercurial Carbonylation Catalysis with Anchored Catalysts.

The reaction of organomercurials with carbon monoxide in the presence of appropriate alcohol to form carboxylic acid derivatives was investigated for a series of anchored palladium and rhodium complexes. All reactions were carried out in a 45 ml stainless steel Parr Reactor equipped for magnet stirring. The temperature of the Parr Reactor was maintained constant by suspension in a temperature regulated oil bath. Standard conditions for each catalyst run were: 4.0 mm phenylmercuric trifluoroacetate, 0.04 mm palladium or rhodium catalyst, 20 ml methanol, 300 psig CO, 75° C., and 0.5 hr. reaction time. The conversion to methyl benzoate was determined by gas chromatography. The results are shown in Table IX.

The data show that the rate of reaction to form methyl benzoate was strongly dependent on the length of the anchoring chain. An increase from dimethylene to octamethylene bridge resulted in a threefold increase of conversion (Sequence Nos. 1 and 2). An increase of the coordination number at the metal resulted in a decreased catalytic activity. For example, L Pd(C$_6$H$_5$CN)PdCl$_2$ is more active than L$_2$PdCl$_2$ (Nos. 4 and 5). In both respects, the carbonylation of arylmercury compounds is similar to the hydroformylation of olefins. However, for the former reaction the mercury byproduct deactivates the anchored catalyst, while good activity maintenance is observed for olefin hydroformylation.

Table IX

Carbonylation of Phenylmercurictrifluoroacetate in the Presence of Methanol with Anchored Silylalkyl Phosphine Rhodium and Palladium Complex Catalysts $$2C_6H_5HgOCOCH_3 + 2CO + 2CH_3OH \xrightarrow[75° C, 30 \text{ min.}]{300 \text{ psig CO}}$$
$$2C_6H_5CO_2CH_3 + [HgOCOCF_3]_2$$

| Sequence No. | Sequence No. in Table V and Table VI | Transition Metal Compound Anchored Phosphine Complex Disregarding HCl Elimination on Anchoring | Yield, Methyl Benzoate % |
|---|---|---|---|
| 1 | 2(V) | [(C$_6$H$_5$)$_2$P(CH$_2$)$_2$SiCl$_3$]$_2$Rh(CO)Cl | 6 |
| 2 | 4(V) | [(C$_6$H$_5$)$_2$P(CH$_2$)$_8$SiCl$_3$]$_2$Rh(CO)Cl | 20 |
| 3 | 1(VI) | (C$_6$H$_5$)$_2$P(CH$_2$)$_8$SiCl$_3$Pd(AcAc)$_2$ | 12 |
| 4 | 2(VI) | [(C$_6$H$_5$)$_2$P(CH$_2$)$_8$SiCl]$_2$PdCl$_2$ | 20 |
| 5 | 3(VI) | (C$_6$H$_5$)$_2$P(CH$_2$)$_8$SiCl$_3$Pd(C$_6$H$_5$CN)Cl$_2$ | 30 |

Example 22 — Catalysis of Hexene Hydroformylation by Anchored Phosphine-Cobalt Complexes The chlorosilylated phosphine (2.17 g, 5 mm) was dissolved in 35 ml of benzene and added slowly with manual mixing to 5 grams (7.5 mm equivalents of silanol) of the cab-o-sil was then transferred to the dessicator-type vessel and transferred under nitrogen to the high-vac-line. The benzene was then removed at room temperature in vacuo; the residue was kept at a pressure of $10^{-4}$ mm for 12 hours. The residual impregnated cab-o-sil was warmed in about 15 minutes to 100° C. At about 80° C. the pressure in the vacuum system increased indicating the evolution of the HCl by-product of the anchoring reaction. Heating was continued at 100° C. for 24 hours. Chlorine analysis of the above treated cab-o-sil gave 4.07% chlorine. The expected quantity of chlorine based on the unreacted phosphine was 14.9%. Therefore, one-third of the chlorosilyl groups of the phosphine must have reacted with the silanol groups of cab-o-sil.

Example 23 — Preparation of the Cobalt Carbonyl Complex of β-(Trichlorosilyl) Ethyl Diphenyl Phosphine

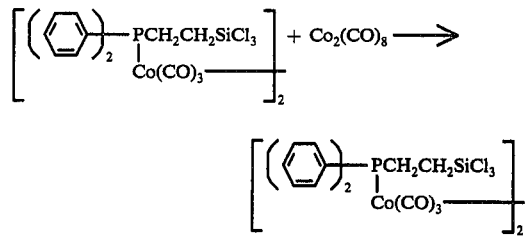

6.35 g (18.6 mm) of Co$_2$(CO) was slurried in 80 ml of benzene in a 500 ml round bottom flask. Then 9.5 g (37.3 mm) of the phosphine in 50 ml of benzene was added in small aliquots to the above mixture. During the addition, a vigorous evolution of carbon monoxide was observed. After the addition the heterogeneous mixture was refluxed for an additional four hours. The flask was stoppered and allowed to stand overnight. The mixture was filtered with suction using a 10–20 μ funnel to remove the unreacted cobalt carbonyl. The residue was washed with benzene and 5 ml of hexane. The combined filtrates were stripped of solvent using a roto-vac to obtain the yellow crystalline residual product. The infrared spectrum (IR) of the complex showed only carbonyl bands expected for an $Co_2(CO)_6L_2$ complex at 2025, 1985, and 1960 cm$^{-1}$.

Analyses calculated for $C_{34}H_{28}P_2Si_2Cl_6O_6Co_2$: C, 41.64; H, 2.85; P, 6.22; Co, 12.03. Found: C, 36.47; H, 2.57; P, 5.77.

Example 24 — Preparation of the Cobalt Carbonyl Complex of Bis-[β-(Trichlorosilyl)] Ethyl Phenyl Phosphine

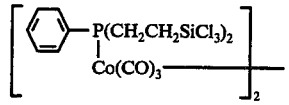

5.95 g (17.3 mm) of $Co_2(CO)_8$ was added to 80 ml of benzene in a 500 ml round bottom flask equipped with a magnetic stirrer. Then 15 g (34.7 mm) of the phosphine were reacted in the manner described in the previous example. A yellow-brown crystalline product was obtained. An IR analysis of the product gave the expected carbonyl stretching frequencies for an $Co_2(CO)_6L_2$ complex at 2020; 1990, and 1960 cm$^{-1}$. The nmr analysis showed the expected α-methylene splitting pattern of the phosphine complex.

Analyses: Calculated for $C_{26}H_{26}P_2Si_4Cl_2O_6Co_2$: C, 27.11; H, 2.26; P, 5.30; Co, 10.24. Found: C, 25.24; H, 2.29; P, 5.05.

Example 25 — Reaction of Anchored Cobalt-Carbonyl Phosphine Complex with 1-Hexene and Water 20 ml 1-hexene (18 mm) and 3.24 ml H$_2$O (18 mm) and enough tetrahydrofuran to make the mixture homogeneous were placed in a reactor vessel equipped with a side arm and teflon stopcock. In the dry box 1.4 g of supported cobalt carbonyl phosphine complex of Table VI, Sequence No. 4 was added to the mixture. The reaction vessel was then closed and heated at 100° C. for 14 hrs. The vessel was then allowed to cool and a sample for g.c. analysis was taken under a nitrogen purge. The anchored catalyst had not undergone any visible change under the above reaction conditions. The g.c. spectrum of the above reaction solution indicated the absence of alcohols, but indicated isomerization of the 1-hexene. The closed reaction vessel was then allowed to react for 3 hrs. at 200° C. The anchored cobalt phosphine carbonyl underwent a gradual visible change from light tan to silver during the heating. The vessel was allowed to cool and a sample for g.c. analysis was taken again under nitrogen purge. The g.c. spectrum of the above solution showed no differences compared to that of the 100° C. reaction condition.

Analysis of anchored catalyst following above reaction: Calculated: P, 3.08. Found: P, 1.81. Analysis of the liquid product mixture for phosphorus gave a value of 110 ppm.

Example 26 — Oxo-Type Reaction of 1-Hexene Catalyzed by the Anchored Catalyst $CH_3(CH_2)_3CH = CH_2 + CO + H_2 \longrightarrow CH_3(CH_2)_2CHO +$
Linear Aldehyde $$CH_3(CH_2)_3\underset{\underset{CH_3}{|}}{CH}\,CHO$$
Branched Aldehyde Into a rocking autoclave were placed 1.5 g of the anchored catalyst of Table VI, Seq. No. 4 and 20 ml of 1-hexene reactant together with 15 ml cyclohexane solvent. This resulted in a reaction mixture containing 1 millimole of catalyst per mole of olefin. The autoclave was then pressured up to 3000 lbs. per in$^2$ pressure with a 2 to 1 pressure ratio of hydrogen and carbon monoxide co-reactants. The temperature was then raised to 200° C. wherein a sharp drop in the pressure indicated that an extremely rapid reaction has occurred. In 15 minutes about 92% of the hexene was converted. Six percent of the reacted olefin was hydrogenated. The rest yielded oxygenated oxo-type products. The oxo-product mixture had a 95 to 5 aldehyde to alcohol ratio and 55% product linearity according to analyses by gas liquid chromatography.

Analysis of the liquid product mixture for phosphorus gave a value less than 20 ppm. Infrared spectroscopy of the carbonyl region indicated the presence of only trace quantities of cobalt carbonyl or cobalt carbonyl phosphine complex. Analysis of anchored catalyst following above reaction: Calculated: P, 3.08, Co, 5.95. Found: P, 1.91, Co, 6.85.

What is claimed is:

1. Anchored silylhydrocarbyl phosphines of the general formula:

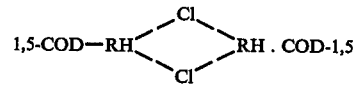

wherein R' is $C_{1-6}$ hydrocarbyl, R is chloro, $C_{1-4}$ acyloxy and $C_{1-6}$ saturated aliphatic or aromatic hydrocarbyl, m is 8 to 30, M is a Group VI to VIII transition metal selected from the group consisting of Fe, Ru, Os, Rh, Ir, Ni, Co, Pd and Pt, X is an anion selected from the group consisting of chloride, bromide and acetate, a ligand selected from the group consisting of 1,5-cyclooctadiene carbonyl, tetrahydrofuran, pyridine, acetonitrile, 1,5,9 cyclododecatriene, x is 1 to 3, y is 1 to 3, n is 2 to 6, z is 1 and 2, g is 1 to 6, t is 0 to 3, wherein anchoring is through Si-O bonds to hydroxyl groups of inorganic solids selected from the groups consisting of silica and metal oxides.

2. The compositions of claim 1 wherein R is selected from the group consisting of methyl, phenyl, chlorine, acyloxy.

3. The compositions of claim 1 wherein the transition metal is of Group VIII.

4. The compositions of claim 1 wherein the inorganic solid is silica.

5. The compositions of claim 1 wherein the inorganic solid is a metal oxide.

6. Anchored silylhydrocarbyl phosphine rhodium complexes of the general formula:

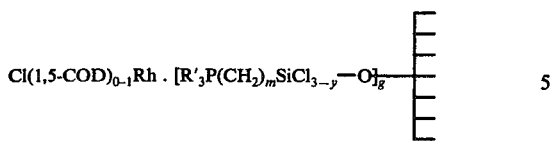

wherein 1,5-COD is 1,5-cyclooctadiene, R' is $C_1$ to $C_{30}$ alkyl, cyclohexyl, phenyl, m is 8 to 30, y is 1 to 3, g is 1 to 3 and the inorganic solid used for anchoring is silica.

7. The compositions of claim 6 wherein g is 1.
8. The compositions of claim 6 wherein g is 3.
9. Anchored silylhydrocarbyl phosphine rhodium complex of the formula:

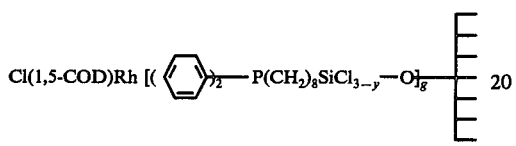

wherein COD is cyclooctadiene, y and g are 1 to 3 wherein anchoring is through Si-O-bonds to hyroxyl groups of inorganic solids selected from the group consisting of silica and metal oxides.

10. A method for heterogeneous Group VI to VIII transition metal hydrocarbyl phosphine complex catalyst preparation comprising the steps of:
   (a) selectively adding silanes of the formula:

wherein R is selected from the group consisting of chlorine, $C_1$ to $C_4$ acyloxy and $C_1$ to $C_6$ saturated aliphatic or aromatic hydrocarbyl, providing that at least one of the R groups is chlorine or $C_1$ to $C_4$ acyloxy, y is 1 or 2, to α-ω dienes of the formula:

$$CH_2=CH(CH_2)_kCH=CH_2$$

wherein k is 4 to 26, to form alkenyl silane monoadducts of the formula:

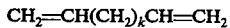

wherein l is k + 2,
(b) adding phosphines of the formula:

wherein R' is selected from the group consisting of a $C_1$ to $C_{30}$ saturated aliphatic or aromatic hydrocarbyl radical, x is 1 or 2, to the alkenyl silane monoadducts of step (a) to form silylhydrocarbyl phosphines of the formula:

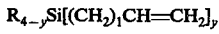

wherein z is 1 or 2 and m is k + 4,
(c) complexing the silylhydrocarbyl phosphines of step (b) with group VI to VIII transition metal compounds of the formula: $MX_n$ wherein M is the metal, X is an anion selected from the group of chloride, bromide and acetate, an organic ligand selected from the group consisting of carbonyl, monoolefins, diolefins, tetrahydrofuran, pyridine, acetonitrile, cyclododecatriene, n is 2 to 6, to form complexes of the formula:

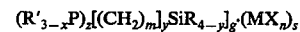

wherein g is 1 to 6 and s is 1 to 3,
(d) anchoring the silylhydrocarbyl phosphines of step (c) and group VI to VIII transition metal complexes thereof as described in step (c) to inorganic solids having surface hydroxyl groups selected from the group consisting of silica and metal oxides, via covalent Si-O-anchoring bonds.

11. A method for heterogeneous Group VI to VIII transition metal hydrocarbyl phosphine complex catalyst preparation comprising the steps of:
   (a) selectively adding silanes of the formula:

wherein R is selected from the group consisting of chlorine, $C_1$ to $C_4$ acyloxy and $C_1$ to $C_6$ saturated aliphatic or aromatic hydrocarbyl, providing that at least one of the R groups is chlorine or $C_1$ to $C_4$ acyloxy, y is 1 or 2 to α, ω-dienes of the formula:

$$CH_2=CH(CH_2)_kCH=CH_2$$

wherein k is 4 to 26 to form alkenyl silane monoadducts of the formula:

wherein l is k + 2,
(b) adding phosphine of the formula:

wherein R' is selected from the group consisting of a $C_1$ to $C_{30}$ saturated aliphatic or aromatic hydrocarbyl radical, x is 1 or 2 to the alkenyl silane monoadducts of step (a) to form silylhydrocarbyl phosphines of the formula:

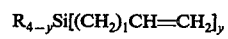

wherein z is 1 or 2 and m is k + 4,
(c) anchoring the silylhydrocarbyl phosphines of step (b) to inorganic solids selected from the group consisting of silicon and metal oxides having hydroxyl groups to form covalent Si-O-anchoring bonds,
(d) complexing the anchored silylhydrocarbyl phosphine-metal oxide product of step (c) with transition metal compounds of the formula: $MX_n$ wherein M is a transition metal selected from the group consisting of Groups VI, VII and VIII, X is an anion selected from the group consisting of chloride, bromide, acetate and organic ligands selected from the group consisting of carbonyl, monoolefins, diolefins, tetrahydrofuran, pyridine, acetonitrile, cyclododecatriene, n is 2 to 6 to form complexes of the formula:

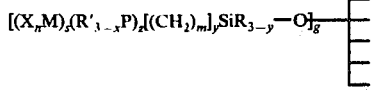

wherein s is 1 to 3 and g is 1 to 6.

12. The method of heterogeneous catalyst preparation of claim 11 wherein the transition metal compound is a member of Group VI – VIII metals consisting of Fe, Ru, Os, Rh, Ir, Ni, Co, Pd and Pt.

13. The method of claim 10 wherein the reactive R group of the silane is chlorine.

14. The method of claim 10 wherein the reactive R group of the silane is acyloxy.

15. The method of claim 10 wherein the R' group of the phosphine is $C_1$ to $C_4$ alkyl, cyclohexyl and phenyl.

16. The method of claim 10 wherein the anchoring is to silica.

17. The method of claim 12 wherein the anchoring is to metal oxides.

18. A method of heterogeneous Group VIII transition metal hydrocarbyl phosphine complex catalyst preparation comprising the steps of:

(a) selectively adding silanes of the formula:

$R_3SiH$ wherein R is chlorine, to $\alpha, \omega$-dienes of the formula:

$CH_2=CH(CH_2)_kCH=CH_2$ wherein k is 4 to 10 to form alkenyl silane monoadducts of the formula:

$R_3Si(CH_2)_lCH=CH_2$ wherein l is $k + 2$, (b) adding phosphines of the formula: $R'_2PH$ wherein R' is $C_1$ to $C_{30}$ alkyl, cyclohexyl, phenyl to the above alkenyl silane to form silylhydrocarbyl phosphines of the formula:

$R_3Si(CH_2)_mPR'_2$ wherein m is $k + 4$, (c) complexing the above silylhydrocarbyl phosphines with Group VIII transition metal compounds of the formula: $MX_n$ wherein M is the metal, X is an anion selected from the group consisting of chloride, bromide and acetate, an organic ligand selected from the group consisting of carbonyl, tetrahydrofuran, pyridine, acetonitrile, 1,5-cyclooctadiene, n is 2 to 6, to form complexes of the formula:

$[R_3Si(CH_2)_mPR'_2]_g \cdot (MX_n)_s$ wherein g is 1 to 6 and s is 1 to 3, (d) anchoring the silylhydrocarbyl phosphines of step (c) and Group VIII transition metal complexes thereof as described in step (C) to silica via covalent Si-O-bonds.

19. A method of heterogeneous Group VIII transition metal hydrocarbyl phosphine complex catalyst preparation comprising the steps of:

(a) selectively adding silanes of the formula:

$R_3SiH$ wherein R is chlorine, to $\alpha, \omega$-dienes of the formula:

$CH_2=CH(CH_2)_kCH=CH_2$ wherein k is 4 to 10 to form alkenyl silane monoadducts of the formula:

$R_3Si(CH_2)_lCH=CH_2$ wherein l is $k + 2$, (b) adding phosphines of the formula $R'_2PH$ wherein R' is $C_1$ to $C_{30}$ alkyl, cyclohexyl, and phenyl to the above alkenyl silane to form silylhydrocarbyl phosphines of the formula:

$R_3Si(CH_2)_mPR'_2$ wherein m is $k + 4$, (c) anchoring the silylhydrocarbyl phosphines of step (b) to silica via covalent Si-O-bonds through the hydroxyl groups on the silica, (d) complexing the anchored silylhydrocarbyl phosphines of step (c) with Group VIII transition metal compounds of the formula: $MX_n$ wherein M is the metal, X is an anion selected from the group consisting of chloride, bromide, acetate and organic ligands selected from the group consisting of carbonyl, tetrahydrofuran, pyridine, acetonitrile, 1,5-cyclooctadiene, n is 2 to 6 to form complexes of the formula:

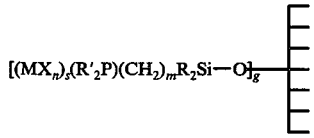

wherein s is 1 to 3 and g is 1 to 6.

20. A method for the preparation of a silylhydrocarbyl phosphine transition metal complex anchored to silica of the formula:

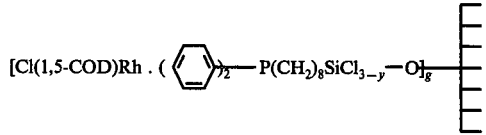

wherein COD is cyclooctadiene, y is 1 to 3, g is 1 to 3 comprising the steps of (a) anchoring a silylhydrocarbyl phosphine of the formula:

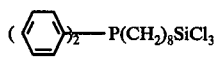

to silica to form a phosphine covalently binded to silica and (b) complexing the anchored phosphine of step (a) of the formula:

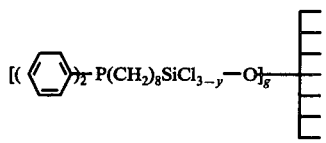
wherein $y$ and $g$ are as previously defined and 1,5-cyclooctadiene rhodium chloride dimer of the formula:
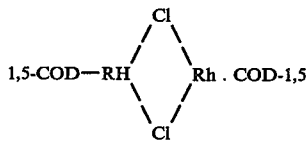
to form the corresponding one-to-one anchored complex.
* * * * *

UNITED STATES PATENT OFFICE
CERTIFICATE OF CORRECTION

Patent No. 4,083,803  Dated April 11, 1978

Inventor(s) Alexis A. Oswald   Lawrence L. Murrell

It is certified that error appears in the above-identified patent and that said Letters Patent are hereby corrected as shown below:

Column 34, Claim 1, lines 37-41, cancel the formula and insert therefor:

$$-- [(X_nM)_t(R'_{3-x}P)_z[(CH_2)_m]_ySiR_{3-y}O]_g --$$

Signed and Sealed this

Sixth Day of November 1979

[SEAL]

Attest:

RUTH C. MASON  
Attesting Officer

LUTRELLE F. PARKER  
Acting Commissioner of Patents and Trademarks